US009463643B2

(12) United States Patent
DeJoseph et al.

(10) Patent No.: US 9,463,643 B2
(45) Date of Patent: Oct. 11, 2016

(54) APPARATUS AND METHODS FOR CONTROLLING APPLICATION OF A SUBSTANCE TO A SUBSTRATE

(75) Inventors: Anthony B. DeJoseph, East Amherst, NY (US); Theodore F. Cyman, Jr., Grand Island, NY (US); Kevin J. Hook, Grand Island, NY (US); Anthony V. Moscato, North Tonawanda, NY (US); Henderikus A. Haan, North Tonawanda, NY (US); John E. Conour, Chicago, IL (US)

(73) Assignee: R.R. Donnelley & Sons Company, Chicago, IL (US)

( * ) Notice: Subject to any disclaimer, the term of this patent is extended or adjusted under 35 U.S.C. 154(b) by 1207 days.

(21) Appl. No.: 13/503,246

(22) PCT Filed: Oct. 22, 2010

(86) PCT No.: PCT/US2010/053830
§ 371 (c)(1),
(2), (4) Date: Jul. 2, 2012

(87) PCT Pub. No.: WO2011/050310
PCT Pub. Date: Apr. 28, 2011

(65) Prior Publication Data
US 2012/0270333 A1 Oct. 25, 2012

Related U.S. Application Data

(60) Provisional application No. 61/254,101, filed on Oct. 22, 2009.

(51) Int. Cl.
*B41J 3/407* (2006.01)
*B01L 3/00* (2006.01)
(Continued)

(52) U.S. Cl.
CPC .......... *B41J 3/407* (2013.01); *B01L 3/502707* (2013.01); *B41J 2/0057* (2013.01); *G01N 35/00009* (2013.01); *B01L 2200/12* (2013.01); *Y10T 436/25375* (2015.01)

(58) Field of Classification Search
CPC ........................................................ G01N 1/18
USPC .......................................................... 436/177
See application file for complete search history.

(56) References Cited

U.S. PATENT DOCUMENTS

| 778,892 A | 1/1905 | Read |
| 1,766,957 A | 6/1930 | Smith |

(Continued)

FOREIGN PATENT DOCUMENTS

| CA | 2 392 730 | 10/2003 |
| CN | 1383992 | 12/2002 |

(Continued)

OTHER PUBLICATIONS

Yue Zhao and Jiyu Fang "Direct Printing of Self-Assembled Lipid Tubules on Substrates" Langmuir 2008, 24, 5113-5117.*

(Continued)

*Primary Examiner* — Christopher A Hixson
*Assistant Examiner* — Emily Berkeley
(74) *Attorney, Agent, or Firm* — McCracken & Gillen LLC

(57) ABSTRACT

Apparatus and methods for controlling application of a substance to a substrate involve the use of a functional agent that helps determine the association of a substance with the substrate. The apparatus and methods may utilize jet technology to apply the functional agent directly to the substrate or to an intermediate surface. The substance may be biological substance or a chemical in nature.

22 Claims, 10 Drawing Sheets

(51) Int. Cl.
*B41J 2/005* (2006.01)
*G01N 35/00* (2006.01)

(56) References Cited

U.S. PATENT DOCUMENTS

| | | |
|---|---|---|
| 2,562,782 A | 7/1951 | Frost |
| 3,574,297 A | 4/1971 | Bozer |
| 3,589,289 A | 6/1971 | Gosnell |
| 3,741,118 A | 6/1973 | Carley |
| 3,790,703 A | 2/1974 | Carley |
| 3,800,699 A | 4/1974 | Carley |
| 3,869,986 A | 3/1975 | Hubbard |
| 3,986,452 A | 10/1976 | Dahlgren |
| 4,010,686 A | 3/1977 | Harris |
| 4,069,759 A | 1/1978 | Endo et al. |
| 4,368,669 A | 1/1983 | Love, III |
| 4,404,907 A | 9/1983 | Kobler et al. |
| 4,718,340 A | 1/1988 | Love, III |
| 4,729,310 A | 3/1988 | Love, III |
| 4,808,443 A | 2/1989 | Minamoto et al. |
| 4,833,486 A | 5/1989 | Zerillo |
| 4,833,530 A | 5/1989 | Kohashi |
| 5,106,414 A | 4/1992 | Kunichika et al. |
| 5,129,321 A | 7/1992 | Fadner |
| 5,188,033 A | 2/1993 | Fadner |
| 5,202,206 A | 4/1993 | Tam |
| 5,221,330 A | 6/1993 | Matsumoto et al. |
| 5,294,946 A | 3/1994 | Gandy et al. |
| 5,312,654 A | 5/1994 | Arimatsu et al. |
| 5,333,548 A | 8/1994 | Fadner |
| 5,336,000 A | 8/1994 | Handa et al. |
| 5,389,958 A | 2/1995 | Bui et al. |
| 5,462,591 A | 10/1995 | Karandikar et al. |
| 5,476,043 A | 12/1995 | Okuda et al. |
| 5,495,803 A | 3/1996 | Gerber et al. |
| 5,501,150 A | 3/1996 | Leenders et al. |
| 5,505,126 A | 4/1996 | Ohno et al. |
| 5,511,477 A | 4/1996 | Adler et al. |
| 5,552,817 A | 9/1996 | Kuehnle |
| 5,554,212 A | 9/1996 | Bui et al. |
| 5,560,608 A | 10/1996 | Silverschotz |
| 5,644,981 A | 7/1997 | Ohno et al. |
| 5,681,065 A | 10/1997 | Rua, Jr. et al. |
| 5,697,297 A | 12/1997 | Rasmussen |
| 5,738,013 A | 4/1998 | Kellett |
| 5,765,083 A | 6/1998 | Shinohara |
| 5,809,893 A | 9/1998 | Gamperling et al. |
| 5,820,932 A | 10/1998 | Hallman et al. |
| 5,826,507 A | 10/1998 | Lim |
| 5,852,975 A | 12/1998 | Miyabe et al. |
| 5,906,156 A | 5/1999 | Shibuya et al. |
| 5,953,988 A | 9/1999 | Vinck |
| 5,966,154 A | 10/1999 | DeBoer |
| 5,969,740 A | 10/1999 | Maeda et al. |
| 6,002,904 A | 12/1999 | Yoshida et al. |
| 6,006,666 A | 12/1999 | Gottling |
| 6,050,193 A | 4/2000 | DeBoer et al. |
| 6,079,331 A | 6/2000 | Koguchi et al. |
| 6,079,806 A | 6/2000 | Koguchi et al. |
| 6,082,263 A | 7/2000 | Koguchi et al. |
| 6,113,231 A | 9/2000 | Burr et al. |
| 6,120,665 A | 9/2000 | Chiang et al. |
| 6,125,750 A | 10/2000 | Achelpohl |
| 6,125,755 A | 10/2000 | Link et al. |
| 6,126,281 A | 10/2000 | Shimoda et al. |
| 6,131,514 A | 10/2000 | Simons |
| 6,152,037 A | 11/2000 | Ishii et al. |
| 6,164,757 A | 12/2000 | Wen et al. |
| 6,173,647 B1 | 1/2001 | Kakuta et al. |
| 6,187,380 B1 | 2/2001 | Hallman et al. |
| 6,196,129 B1 | 3/2001 | Kellett |
| 6,231,177 B1 | 5/2001 | Cherukuri et al. |
| 6,283,031 B1 | 9/2001 | Kakuta et al. |
| 6,283,589 B1 | 9/2001 | Gelbart |
| 6,295,928 B1 | 10/2001 | Heinzl et al. |
| 6,298,780 B1 | 10/2001 | Ben-Horin et al. |
| 6,315,916 B1 | 11/2001 | Deutsch et al. |
| 6,318,264 B1 | 11/2001 | D'Heureuse et al. |
| 6,341,559 B1 | 1/2002 | Riepenhoff et al. |
| 6,354,207 B1 | 3/2002 | Maekawa et al. |
| 6,367,380 B1 | 4/2002 | Whelan |
| 6,386,696 B1 | 5/2002 | Rodi et al. |
| 6,393,980 B2 | 5/2002 | Simons |
| 6,402,317 B2 | 6/2002 | Yanagawa et al. |
| 6,416,175 B2 | 7/2002 | Furukawa et al. |
| 6,422,696 B1 | 7/2002 | Takahashi et al. |
| 6,439,713 B1 | 8/2002 | Noguchi et al. |
| 6,470,799 B2 | 10/2002 | Nakazawa et al. |
| 6,477,948 B1 | 11/2002 | Nissing et al. |
| 6,520,087 B2 | 2/2003 | Heinzl et al. |
| 6,526,886 B2 | 3/2003 | Loccufier et al. |
| 6,536,873 B1 | 3/2003 | Lee et al. |
| 6,539,856 B2 | 4/2003 | Jones et al. |
| 6,543,360 B2 | 4/2003 | Sasaki et al. |
| 6,558,458 B1 | 5/2003 | Gloster |
| 6,566,039 B1 | 5/2003 | Teng |
| 6,585,367 B2 | 7/2003 | Gore |
| 6,595,631 B2 | 7/2003 | Tanikawa et al. |
| 6,634,295 B1 | 10/2003 | Newington et al. |
| 6,644,183 B2 | 11/2003 | Takasawa et al. |
| 6,648,468 B2 | 11/2003 | Shinkoda et al. |
| 6,652,631 B2 | 11/2003 | Itakura |
| 6,662,723 B2 | 12/2003 | Loccufier et al. |
| 6,679,170 B2 | 1/2004 | Mori |
| 6,699,640 B2 | 3/2004 | Verschueren et al. |
| 6,736,500 B2 | 5/2004 | Takahashi et al. |
| 6,739,260 B2 | 5/2004 | Damme et al. |
| 6,745,693 B2 | 6/2004 | Teng |
| 6,758,140 B1 | 7/2004 | Szumla et al. |
| 6,772,687 B2 | 8/2004 | Damme et al. |
| 6,779,444 B2 | 8/2004 | Hauptmann et al. |
| 6,780,305 B2 | 8/2004 | Nishino et al. |
| 6,783,228 B2 | 8/2004 | Szumla et al. |
| 6,815,075 B2 | 11/2004 | Kasai et al. |
| 6,815,366 B2 | 11/2004 | Higuchi |
| 6,823,789 B2 | 11/2004 | Hara et al. |
| 6,851,363 B2 | 2/2005 | Schneider |
| 6,852,363 B2 | 2/2005 | Loccufier et al. |
| 6,862,992 B2 | 3/2005 | Nakazawa et al. |
| 6,906,019 B2 | 6/2005 | Nitzan et al. |
| 6,918,663 B2 | 7/2005 | Schaschek et al. |
| 6,935,735 B2 | 8/2005 | Tanikawa et al. |
| 6,983,693 B2 | 1/2006 | Simons |
| 7,070,269 B2 | 7/2006 | Tanikawa et al. |
| 7,191,703 B2 | 3/2007 | Dilling |
| 7,191,705 B2 | 3/2007 | Berg et al. |
| 7,240,998 B2 | 7/2007 | Murakami et al. |
| 7,281,790 B2 | 10/2007 | Mouri et al. |
| 7,311,396 B2 | 12/2007 | Kwon et al. |
| 7,523,704 B2 | 4/2009 | Domotor |
| 7,691,280 B2 | 4/2010 | Waldrop et al. |
| 7,959,278 B2 | 6/2011 | Regan et al. |
| 2001/0020964 A1 | 9/2001 | Irihara et al. |
| 2001/0022596 A1 | 9/2001 | Korol |
| 2001/0040615 A1 | 11/2001 | Beauchamp et al. |
| 2001/0042460 A1 | 11/2001 | Yoshida |
| 2002/0001004 A1 | 1/2002 | Mantell et al. |
| 2002/0014169 A1 | 2/2002 | Siler et al. |
| 2002/0017209 A1 | 2/2002 | Gutfleisch et al. |
| 2002/0038611 A1 | 4/2002 | Naniwa et al. |
| 2002/0043171 A1 | 4/2002 | Loccufier et al. |
| 2002/0056388 A1 | 5/2002 | Makino |
| 2002/0100383 A1 | 8/2002 | McPherson et al. |
| 2002/0104455 A1 | 8/2002 | Deutsch et al. |
| 2002/0139268 A1 | 10/2002 | Emery et al. |
| 2002/0154188 A1 | 10/2002 | Hiyane et al. |
| 2002/0170451 A1 | 11/2002 | Nakazawa et al. |
| 2003/0047688 A1* | 3/2003 | Faris et al. ................ 250/432 R |
| 2003/0089261 A1 | 5/2003 | Landsman |
| 2003/0103093 A1 | 6/2003 | Vanhooydonck |
| 2003/0128249 A1 | 7/2003 | Booth |
| 2003/0128250 A1 | 7/2003 | Booth |
| 2003/0153649 A1 | 8/2003 | Bromberg |
| 2003/0159607 A1 | 8/2003 | Nitzan et al. |

(56) References Cited

U.S. PATENT DOCUMENTS

| | | |
|---|---|---|
| 2003/0210298 A1 | 11/2003 | Madeley |
| 2003/0210314 A1 | 11/2003 | Palmer et al. |
| 2004/0053011 A1 | 3/2004 | Behm et al. |
| 2004/0085395 A1 | 5/2004 | Madeley |
| 2004/0089179 A1 | 5/2004 | Link |
| 2004/0090508 A1 | 5/2004 | Chowdry et al. |
| 2004/0090516 A1 | 5/2004 | Gruetzmacher et al. |
| 2004/0103801 A1 | 6/2004 | Miller et al. |
| 2004/0103803 A1 | 6/2004 | Price et al. |
| 2004/0106696 A1 | 6/2004 | Ma et al. |
| 2004/0109055 A1 | 6/2004 | Pan et al. |
| 2004/0129158 A1 | 7/2004 | Figov et al. |
| 2004/0135276 A1 | 7/2004 | Nielsen et al. |
| 2004/0154489 A1 | 8/2004 | Deutsch et al. |
| 2004/0177784 A1 | 9/2004 | Yamamoto et al. |
| 2004/0182270 A1 | 9/2004 | Wiedemer et al. |
| 2004/0187720 A1 | 9/2004 | Naniwa et al. |
| 2004/0250836 A1 | 12/2004 | Koppelkamm et al. |
| 2005/0028696 A1 | 2/2005 | Price et al. |
| 2005/0056169 A1 | 3/2005 | Hashimoto et al. |
| 2005/0115429 A1 | 6/2005 | Link |
| 2005/0122355 A1 | 6/2005 | Kanda et al. |
| 2005/0181187 A1 | 8/2005 | Vosseler et al. |
| 2005/0204945 A1 | 9/2005 | Sonokawa |
| 2005/0211130 A1 | 9/2005 | Watanabe |
| 2005/0223927 A1 | 10/2005 | Wiedemer |
| 2005/0270351 A1 | 12/2005 | Mouri et al. |
| 2006/0011817 A1 | 1/2006 | Harush et al. |
| 2006/0040210 A1 | 2/2006 | Eck et al. |
| 2006/0066704 A1 | 3/2006 | Nishida |
| 2006/0075916 A1 | 4/2006 | Edwards et al. |
| 2006/0075917 A1 | 4/2006 | Edwards |
| 2006/0077243 A1 | 4/2006 | Edwards |
| 2006/0077244 A1 | 4/2006 | Edwards |
| 2006/0132566 A1 | 6/2006 | Desie et al. |
| 2006/0201361 A1 | 9/2006 | Wiedemer |
| 2006/0284951 A1 | 12/2006 | Ikeda et al. |
| 2007/0062389 A1 | 3/2007 | Link |
| 2007/0068404 A1 | 3/2007 | Hirahara et al. |
| 2007/0137509 A1 | 6/2007 | Fork |
| 2007/0164559 A1 | 7/2007 | Kozdras |
| 2007/0199457 A1 | 8/2007 | Cyman et al. |
| 2007/0199458 A1 | 8/2007 | Cyman et al. |
| 2007/0199459 A1 | 8/2007 | Cyman et al. |
| 2007/0199460 A1 | 8/2007 | Cyman et al. |
| 2007/0199461 A1 * | 8/2007 | Cyman, Jr. ............ B41C 1/105 101/211 |
| 2007/0199462 A1 | 8/2007 | Cyman et al. |
| 2007/0199469 A1 | 8/2007 | Zahn |
| 2007/0200794 A1 | 8/2007 | Mueller et al. |
| 2007/0204755 A1 | 9/2007 | Moreau |
| 2007/0227383 A1 | 10/2007 | Decre et al. |
| 2007/0240593 A1 | 10/2007 | Schneider et al. |
| 2008/0271627 A1 | 11/2008 | Teng |
| 2009/0056577 A1 | 3/2009 | Hook et al. |
| 2009/0056578 A1 | 3/2009 | DeJoseph et al. |
| 2009/0064884 A1 | 3/2009 | Hook et al. |
| 2009/0064886 A1 | 3/2009 | Hook et al. |
| 2009/0213201 A1 | 8/2009 | Numata et al. |

FOREIGN PATENT DOCUMENTS

| | | |
|---|---|---|
| DE | 4327212 | 2/1995 |
| DE | 10245066 | 4/2003 |
| EP | 101 266 | 2/1984 |
| EP | 0126479 | 11/1984 |
| EP | 0588399 | 3/1994 |
| EP | 0590164 | 4/1994 |
| EP | 0601531 | 6/1994 |
| EP | 0646458 | 4/1995 |
| EP | 0965444 | 6/1998 |
| EP | 0882584 | 12/1998 |
| EP | 0883026 | 12/1998 |
| EP | 0911154 | 4/1999 |
| EP | 0911155 | 4/1999 |
| EP | 0936064 | 8/1999 |
| EP | 1 118 470 | 7/2001 |
| EP | 1 118 471 | 7/2001 |
| EP | 1 118 472 | 7/2001 |
| EP | 1170122 | 1/2002 |
| EP | 1177514 | 2/2002 |
| EP | 1177914 | 2/2002 |
| EP | 1 426 193 | 6/2004 |
| EP | 1 522 404 | 4/2005 |
| EP | 1 547 793 | 6/2005 |
| JP | 53-15905 | 2/1978 |
| JP | 56-105960 | 8/1981 |
| JP | 56-113456 | 9/1981 |
| JP | 58-217567 | 12/1983 |
| JP | 62-025081 | 2/1987 |
| JP | 63-109052 | 5/1988 |
| JP | 63-125534 | 8/1988 |
| JP | 02-098482 | 4/1990 |
| JP | 2-98482 | 4/1990 |
| JP | 02-269094 | 11/1990 |
| JP | 4-69244 | 3/1992 |
| JP | 4-97236 | 3/1992 |
| JP | 4-97848 | 3/1992 |
| JP | 06-206297 | 7/1994 |
| JP | 6-225081 | 8/1994 |
| JP | 6-270380 | 9/1994 |
| JP | 8-310101 | 11/1996 |
| JP | 08-310151 | 11/1996 |
| JP | 9-85929 | 3/1997 |
| JP | 09-267549 | 10/1997 |
| JP | 10-235989 | 9/1998 |
| JP | 10-286939 | 10/1998 |
| JP | 2946201 | 10/1998 |
| JP | 11-302585 | 11/1999 |
| JP | 11-320865 | 11/1999 |
| JP | 2002-536462 | 8/2000 |
| JP | 2000-272261 | 10/2000 |
| JP | 2001-212956 | 8/2001 |
| JP | 2001-225437 | 8/2001 |
| JP | 2002-127354 | 5/2002 |
| JP | 2002-326455 | 11/2002 |
| JP | 2002-361833 | 12/2002 |
| JP | 2003-25554 | 1/2003 |
| JP | 2003-080664 | 3/2003 |
| JP | 2003-80816 | 3/2003 |
| JP | 2003-237220 | 8/2003 |
| JP | 2004-050575 | 2/2004 |
| JP | 2004-66816 | 3/2004 |
| JP | 2004-98682 | 4/2004 |
| JP | 2004-181955 | 7/2004 |
| JP | 2004-299167 | 10/2004 |
| JP | 2005-059458 | 3/2005 |
| JP | 2005-074693 | 3/2005 |
| JP | 3756943 | 3/2005 |
| JP | 2005-313490 | 11/2005 |
| WO | WO 94/11191 | 5/1994 |
| WO | WO 99/17938 | 4/1999 |
| WO | WO 01/34394 | 5/2001 |
| WO | WO 01/49506 | 7/2001 |
| WO | WO 01/54915 | 8/2001 |
| WO | WO 2004/039586 | 5/2004 |
| WO | WO 2007/071551 | 6/2007 |
| WO | WO 2009025821 A1 * | 2/2009 ............ B41M 1/06 |

OTHER PUBLICATIONS

International Preliminary Report on Patentability dated Sep. 4, 2008, International Application No. PCT/US2007/004437 International filing date Feb. 21, 2007.

International Preliminary Report on Patentability dated Sep. 4, 2008, International Application No. PCT/US2007/004441 International filing date Feb. 21, 2007.

International Preliminary Report on Patentability dated Sep. 4, 2008, International Application No. PCT/US2007/004440 International filing date Feb. 21, 2007.

International Preliminary Report on Patentability dated Sep. 4, 2008, International Application No. PCT/US2007/004438 International filing date Feb. 21, 2007.

(56) References Cited

OTHER PUBLICATIONS

International Preliminary Report on Patentability dated Sep. 4, 2008, International Application No. PCT/US2007/004444 International filing date Feb. 21, 2007.
International Preliminary Report on Patentability dated Sep. 4, 2008, International Application No. PCT/US2007/004442 International filing date Feb. 21, 2007.
International Search Report and Written Opinion in PCT/US2008/009910 dated Jan. 20, 2009.
Search Report in EP 08 00 6593 dated Jan. 12, 2009.
Search Report in EP 08 00 6594 dated Jan. 12, 2009.
Gloster et al., Abstract of "Direct Computer to Plate Printing," *Society for Imaging Science and Technology*, Oct. 2001, 1 page.
Nobuhiro et al., Abstract of "Application of Solid Ink Jet Technology to a Direct Plate Maker," *Science Links Japan*, 1999, 1 page.
Katherine O'Brien, "CTP in Small Packages," *American Printer*, Sep. 1, 1998, 4 pages.
U.S. Appl. No. 60/775,511, Inventors Cyman, Jr. et al., filed Feb. 21, 2006.
U.S. Appl. No. 60/819,301, Inventors Cyman, Jr. et al., filed Jul. 7, 2006.
Letter to EPO dated Nov. 30, 2010, with attachments, EP Application No. 07-751-214.3, Applicant Moore Wallace North America, Inc.
Letter to EPO dated Dec. 7, 2010, with attachments, EP Application No. 08-006-593.1, Applicant Moore Wallace North America, Inc.
EPO Office Action dated Oct. 1, 2010, EP Application No. 08-006-593.1, Applicant Moore Wallace North America, Inc.
EPO Office Action dated Jul. 28, 2010, EP Application No. 07-751-214.3, Applicant Moore Wallace North America, Inc.
Letter to EPO dated Aug. 12, 2010 with attachment, EP Application No. 08-006-593.1, Applicant Moore Wallace North America, Inc.
Letter to EPO dated Jul. 19, 2010 with attachment, EP Application No. 08828001.1, Applicant Moore Wallace North America, Inc.
EPO Office Action dated Jul. 28, 2010, EP Application No. 08-006-593.1, Applicant Moore Wallace North America, Inc.
Letter from Mr. Qi Xue regarding Second Office Action from Chinese Patent Office dated Nov. 29, 2010, Chinese Patent Application No. 200780006170.9, Applicant Moore Wallace North America, Inc.
Second Office Action dated Nov. 3, 2010, with English translation attached, Chinese Patent Application No. 200780006170.9, Applicant Moore Wallace North America, Inc.
Letter to Mr. Qi Xue dated Jan. 4, 2011, Chinese Patent Application No. 200780006170.9, Applicant Moore Wallace North America, Inc.
Letter from Mr. Qi Xue dated Jan. 7, 2011, Chinese Patent Application No. 200780006170.9, Applicant Moore Wallace North America, Inc.
Letter to Mr. Qi Xue dated Jan. 12, 2011 regarding Jan. 7, 2011 communication, Chinese Patent Application No. 200780006170.9, Applicant Moore Wallace North America, Inc.
Letter from Mr. Qi Xue dated Jan. 13, 2011, Chinese Patent Application No. 200780006170.9, Applicant Moore Wallace North America, Inc.
Letter to Mr. Qi Xue dated Jan. 12, 2011 regarding Jan. 12, 2011 communication, Chinese Patent Application No. 200780006170.9, Applicant Moore Wallace North America, Inc.
Letter from Mr. Qi Xue dated Jan. 18, 2011 regarding Second Office Action Response, Chinese Patent Application No. 200780006170.9, Applicant Moore Wallace North America, Inc.
Second Office Action Response dated Jan. 18, 2011, with English translation attached, Chinese Patent Application No. 200780006170.9, Applicant Moore Wallace North America, Inc.
Email to Mr. Qi Xue dated Mar. 9, 2011, with substitute Response to Second Office Action attached, Chinese Patent Application No. 200780006170.9, Applicant Moore Wallace North America, Inc.
www.flickr.com, "MacWorld Magazine: Cover Art Woes", website, http://www.flickr.com/photos/66071596@N00/3964123486/ (printed on Mar. 8, 2011).
www.livedocs.adobe.com, "Fill a selection or layer with a color", website, http://livedocs.adobe.com/en_US/Photoshop/10.0/help.html?content=WSfd1234e1c4b69f30ea53e41001031ab64-77d4.html (printed on Mar. 8, 2011).
www.magazinepublisher.com, "Mailing Magazines", website, http://www.magazinepublisher.com/mailing.html (printed on Mar. 8, 2011).
www.printindustry.com, "Magazine Cover Wraps", website, http://www.printindustry.com/Newsletters/Newsletter---67.aspx (printed on Mar. 8, 2011).
www.mdprint.com, "M&D Printing Periodical Co-mailing Template Inkjet Knockout Version", available at http://www.mdprint.com/knockout%20template.pdf, (printed on Mar. 8, 2011).
www.riponprinters.com, "Designing Your Mailpiece for Inkjet Addressing", available at http://www.riponprinters.com/tech---library/pdf/M7_TLines_Design_for_Inkjet.pdf (printed on Mar. 8, 2011).
www.malanenewman.com, "Graphic Design Terminology", website, available at http://www.malanenewman.com/graphic_design_terminology.html (printed on Mar. 8, 2011).
International Search Report and Written Opinion in PCT/US2010/053830 dated Dec. 27, 2010.
EPO Communication under Rule 71(3) EPC dated Jan. 10, 2011, with attached examiner's amendments, European Patent Appl. No. 07751211.9, Applicant Moore Wallace North America, Inc.
Second email to Mr. Qi Xue dated Mar. 9, 2011, with revised substitute Response to Second Office Action attached, Chinese Patent Application No. 200780006170.9, Applicant Moore Wallace North America, Inc.
European Patent Office Search Report & Written Opinion, EP 11 17 1598 dated Sep. 14, 2011.
Office Action dated Dec. 27, 2011, for JP Patent Application No. 2008-556392, with English translation attached, Applicant, Moore Wallace North America, Inc., (5 pages).
EP Search Report and English translation, dated Jan. 5, 2012, for European Patent Application No. EP 11 18 4552, Applicant, Moore Wallace North America, Inc., (7 pages).
Office Action dated Jan. 24, 2012, for JP Patent Application No. 2008-556392, with English translation attached, Applicant, Moore Wallace North America, Inc., (7 pages).
Second Office Action dated Feb. 16, 2012, for CN Patent Application No.2008-80113100.8, Applicant, Moore Wallace North America, Inc., (6 pages).
Letter dated Nov. 2, 2011 to Arochi, Marroquin & Lindner, S.C.
Letter dated Nov. 25, 2011 from Arochi, Marroquin & Lindner, S.C.
Int'l. Search Report and Written Opinion dated Dec. 2, 2011 for International Application No. PCT/US2011/051975.
Response, dated Apr. 11, 2012, to European Patent Office Search Report and Written Opinion, dated Sep. 9, 2011, (3 pages), European Patent Application No. 11171598.3, Applicant Moore Wallace North America Inc.
Letter dated Apr. 4, 2012 to Mr. Fujio Sasajima regarding Japanese Patent Application No. 2008-556392 (2 pages).
Email dated Apr. 20, 2012 to Mr. Fujio Sasajima regarding Japanese Patent Application No. 2008-556392 (1 page).
Letter dated Apr. 24, 2012 from Mr. Fujio Sasajima regarding Japanese Patent Application No. 2008-556392 (1 page).
Letter dated Apr. 19, 2012 to Mr. Qi Xue regarding Chinese Patent Application No. 2008801133100.8 (3 pages).
Letter dated May 3, 2012 from Mr. Qi Xue regarding Chinese Patent Application No. 2008801133100.8 (1 page).
European Patent Office Response dated Dec. 4, 2012 for European Patent Application 11171598.3, Applicant, Moore Wallace North America Inc. (4 pages).
European Patent Office Response dated Dec. 18, 2012 for European Patent Application 11171598.3, Applicant, Moore Wallace North America Inc. (2 pages).
Japanese Patent Office Action dated Oct. 23, 2012 for Japanese Patent Application 2010-521872, with English translation attached, Applicant, Moore Wallace North America Inc. (6 pages).
Japanese Patent Office Action dated Oct. 2, 2012, for Japanese Patent Application 2010-521871, with English translation attached, Applicant, Moore Wallace North America Inc. (9 pages).

(56) References Cited

OTHER PUBLICATIONS

English translation of Japanese Patent Application JP 4-97848, Applicant, Mitsubishi Heavy Industries KK. (9 pages).
Amendment/Instructions to Japanese associate dated Jan. 9, 2013 and confirmation of Amendment filing dated Jan. 23, 2013 (9 pages).
Boland, T. et al., "Cell and Organ Printing 2: Fusion of Cell Aggregates in Three-Dimensional Gels", The Anatomical Record Part A (2003), 2003 Wiley-Liss, Inc., pp. 497-502, (6 pages).
"High Performance Liquid Chromatography," Wikipedia; http://en.wikipedia.ord/wiki/HPLC, printed Oct. 3, 2007 (5 pages).
Mosher, Dave, "Inkjets Print Living Cells in 3-D," http://www.msnbc.msn.com/id/21253196, printed Oct. 15, 2007 (4 pages).
Roth, E.A. et al., "Inkjet Printing for High-Throughput Cell Patterning," Biomaterials, vol. 25 (2004), pp. 3707-3715, Oct. 20, 2003 (9 pages).
Abaxis Medical Diagnostics, "Piccolo® xpress: On-The-Spot Chemistry Results in minutes", http://www.abaxis.com/medical/piccolo.html; printed Oct. 24, 2007 (2 pages).
Calvert, Paul, "Printing Cells," printed Jul. 22, 2008, from www.sciencemag.org; Oct. 12, 2007, vol. 318, Science, pp. 208-209 (2 pages).
Symyx, "Symyx Tools," http://www.symyx.com/page.php?id=50, printed Oct. 24, 2007 (1 page).
European Patent Office Int'l Search Report for PCT/US2008/009901 dated Nov. 4, 2008, Applicant, R.R. Donnelley, (14 pages).
European Patent Office Int'l Search Report for PCT/US2008/009911 dated Oct. 23, 2008, Applicant, R.R. Donnelley, (12 pages).
Second Office Action dated Apr. 6, 2011, with English translation attached, Chinese Patent Application No. 200780006171.3, Applicant, Moore Wallace North America, Inc., (7 pages).
Letter to Mr. Qi Xue dated May 12, 2011, with claim amendments attached, Chinese Patent Application No. 200780006171.3, Applicant, Moore Wallace North America, Inc., (4 pages).
Letter from Mr. Qi Xue dated Jun. 8, 2011, Chinese Patent Application No. 200780006171.3, Applicant, Moore Wallace North America, Inc., (1 page).
Office Action dated Aug. 30, 2011 from Mexican Institute of Industrial Property, File No. MX/a/2010/001992, Applicant, Moore Wallace North America, Inc., with English translation attached, (4 pages).
English Translation of Office Action for Korean Application No. 10-2008-7022776 dated Apr. 26, 2013 (2 pages).
Letter to You Me Patent & Law Firm dated May 31, 2013 regarding proposed response to Office action for Korean Application No. 10-2008-7022776 (2 pages).
E-mail to You Me Patent & Law Firm dated Jun. 21, 2013 regarding proposed Response for Korean Application No. 10-2008-7022776 (2 pages).
Letter from You Me Patent & Law Firm dated Jun. 27, 2013 regarding proposed Response for Korean Application No. 10-2008-7022776 (1 page).
Office Action Response and English translation of Claim amendments filed Jun. 24, 2013 for Korean Application No. 10-2008-7022776 (11 pages).
U.S. Appl. No. 61/278,915, Inventors DeJoseph, et al., filed Oct. 14, 2009.
International Preliminary Report on Patentability and Written Opinion for PCT/US2008/009893, dated Mar. 4, 2010.
Response letter to EPO for Appl. No. 08-006-593.1-1251, dated Feb. 8, 2010, and attached amendments.
Lamont Wood, 3-D Home Printers Could Change Economy Oct. 11, 2007, URL: http://www/msnbc.msn.com/id/21252137/, (2 pages).
W. Shen et al., "A New Understanding on the Mechanism of Fountain Solution in the Prevention of Ink Transfer to the Non-image Area in Conventional Offset Lithography", J. Adhesion Sci. Technol., vol. 18, No. 15-16, pp. 1861-1887, (2004), (27 pages).
Air Products, Surfynol® 400 Series Surfactants, (3 pages).

"Amine Ethoxylates," (Jun. 26, 2008), URL: http://www.huntsman.com/performance_products/Index.cfm?PageID=5723&PrintPage=1&Showtitle=1, (1 page).
"Effect of Polyether Monoamine Structure on Pigment Dispersant Properties," (Feb. 2, 2009), Paint & Coatings Industry, (Mar. 1, 2006), URL: http://www.accessmylibrary.com/comsite5/bin/aml_landing_tt.pl?purchase_type=ITM & tem . . . , (5 pages).
R. Steitz et al., "Experimental Report: Does the Chemical Nature of the Substrate Trigger Net Adsorption of Pluronic F127?", BENSC, (Jan. 15, 2003), (1 page).
BASF,Key Features & Benefits, Joncryl® 50, (2 pages); Joncryl® 52 (2 pages); Joncryl® 60 (2 pages); Joncryl® 61 (2 pages); Joncryl® 678 (3 pages); Joncryl® 682 (3 pages), (Mar. 23, 2007).
Polyethylenimines (General Information), (3 pages).
Nissan Chemical—Colloidal Silica, "Snowtex®", URL: http://www.nissanchem-usa.com/snowtex.php, (Jun. 26, 2008), (8 pages).
BASF Corporation 1999, Table of Contents, (37 pages).
BASF Corporation 2002 Technical Bulletin, "Pluronic® F127 Block Copolymer Surfactant", (1 page).
Huntsman Corporation 2005 Technical Bulletin, "Surfonic® T-2 Surfactant", (2 pages).
Huntsman Corporation 2007 Technical Bulletin, "The Use of Surfonamine® Amines in Ink and Pigment Applications", (5 pages).
"Amendment of the Claims" for PCT/US2008/009893 dated Mar. 20, 2009, (2 pages).
"Amendment of the Claims" for PCT/US2008/009910 dated Mar. 19, 2009, (3 pages).
EPO Office Action for Appl. No. 077-751-211.9-1251, dated Sep. 22, 2009, and attached Jul. 1, 2009 letter to EPO and amendments.
Response letter to EPO for Appl. No. 077-751-211.9-1251, dated Jan. 29, 2010, and attached amendments.
EPO Office Action for Appl. No. 077-751-214.3-1251, dated Aug. 3, 2009, and attached Jul. 1, 2009 letter to EPO and amendments.
Response letter to EPO for Appl. No. 077-751-214.3-1251, dated Oct. 21, 2009.
EPO Office Action for Appl. No. 077-751-214.3-1251, dated Dec. 10, 2009, and attached Jul. 1, 2009 letter to EPO and amendments.
Response letter to EPO for Appl. No. 077-751-214.3-1251, dated Mar. 31, 2010, and attached amendments.
EPO Office Action for Appl. No. 08-006-593.1-1251, dated Oct. 8, 2009.
International Search Report and Written Opinion for PCT/US2008/009893 dated Jan. 23, 2009.
Response letter to EPO for Appl. No. 08006594.9, dated Nov. 26, 2009, and attached amendments and EP search report 08006594 Jan. 12, 2009.
International Preliminary Report on Patentability and Written Opinion for PCT/US2008/009910 dated Mar. 4, 2010.
International Preliminary Report on Patentability and Written Opinion for PCT/US2008/009901 dated Mar. 4, 2010.
H. Kipphan: "Handbook of Print Media" 2001, Springer, Berlin, XP002446641, p. 52-55.
International Search Report and Written Opinion, International Application No. PCT/US2007/004444 dated Aug. 28, 2007.
International Preliminary Report on Patentability and Written Opinion, for PCT/US2008/009911 dated Mar. 4, 2010.
3rd Supplemental Information Disclosure Statement & Interview Summary dated, Apr. 28, 2010 for U.S. Appl. No. 11/709,396.
International Search Report and Written Opinion, International Application No. PCT/US2007/004437 dated Sep. 3, 2007.
International Search Report and Written Opinion, International Application No. PCT/US2007/004440 dated Aug. 28, 2007.
International Search Report and Written Opinion, International Application No. PCT/US2007/004438 dated Aug. 28, 2007.
International Search Report and Written Opinion, International Application No. PCT/US2007/004441 dated Aug. 28, 2007.
International Search Report and Written Opinion, International Application No. PCT/US2007/004442 dated Aug. 28, 2007.

\* cited by examiner

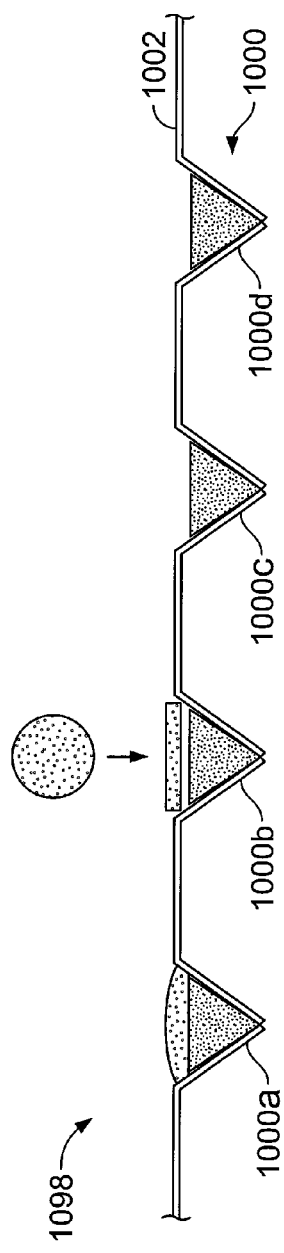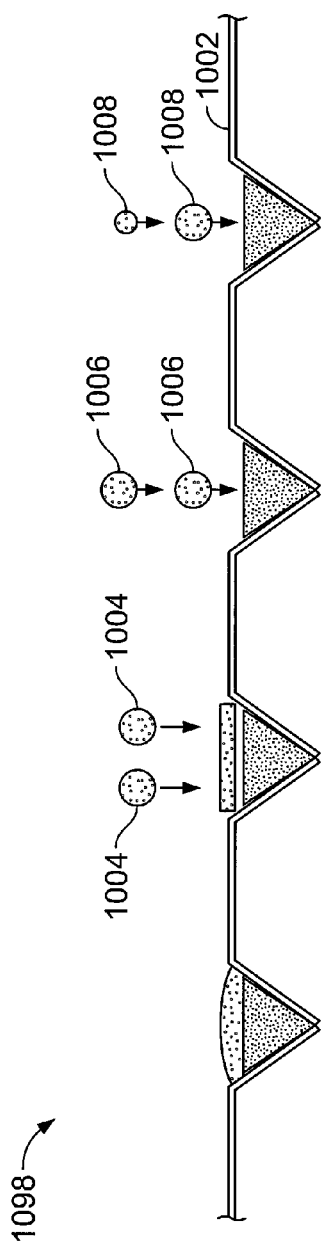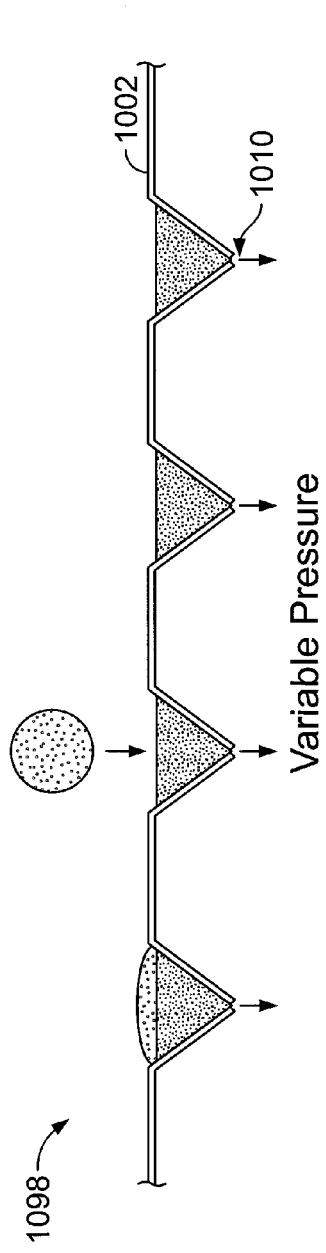

APPARATUS AND METHODS FOR CONTROLLING APPLICATION OF A SUBSTANCE TO A SUBSTRATE

CROSS-REFERENCE TO RELATED APPLICATIONS

The present application is the national phase entry of PCT Patent Application No. PCT/US2010/053830, filed Oct. 22, 2010, which claims the benefit of provisional U.S. Patent Application Ser. No. 61/254,101, filed Oct. 22, 2009. The entire contents of both of these applications are incorporated herein by reference.

The present application is also related to U.S. Pat. Nos. 8,011,300 and 8,961,270, issued Sep. 6, 2011 and Nov. 22, 2011, respectively. In addition, this application is related to U.S. patent application Ser. Nos. 11/709,497, 11/709,599, 11/709,555, and 11/709,396, all of which were filed on Feb. 21, 2007, and provisional U.S. patent application Ser. Nos. 60/775,511 and 60/819,301 filed on Feb. 21, 2006, and Jul. 7, 2006, respectively. In addition, the present application is related to provisional U.S. Patent Application Ser. Nos. 60/965,361, filed Aug. 20, 2007; 60/965,634, filed Aug. 21, 2007; 60/965,753, filed Aug. 22, 2007; 60/965,861, filed Aug. 23, 2007; 60/965,744, filed Aug. 22, 2007 and 60/965,743, filed Aug. 22, 2007. The entire contents of all of the above-listed patents and applications are incorporated herein by reference.

BACKGROUND

Ink jet printing technology provides printers with variable capability of printing ink. There are several jetting technologies including thermal (such as, bubble jet) and piezoelectric that are used in ink jet printing. In this context, tiny droplets of ink are ejected from a printing head and deposited onto a page. In a thermal jet head, a heat source vaporizes a substance, such as ink to create a bubble. The expanding bubble causes a droplet to form, and the droplet is ejected from the head. Piezoelectric technology uses a piezo material. Application of an electric potential to the piezo material causes a warping of the piezo material to increase the pressure in the head, and thus eject a drop of a substance from the nozzle. The drop is emitted from a tiny hole in the jet cartridges. The cartridges may contain any number of nozzles. For example, the jet cartridges may have six hundred holes, arranged in two rows of three hundred, or any other configuration and/or number of holes, as needed.

The adoption of jet-based patterning techniques has been found to be useful in the production of other articles of manufacture including electrical components, such as transistors and other devices. Still further, indicia or other markings have been printed on substrates other than paper, such as plastic film, metal substrates, and the like.

Jetting technology has also been used to deposit live cells and extracellular matrix proteins for forming cell patterns on substrates (Calvert, Science 318 (Oct. 12, 2007), 208-209; Roth et al., Biomaterials 25 (2004), 3707-3715). Thus, the utility of jetting technology is being realized in new fields of endeavor. Further innovation utilizing jet-based technologies may prove to play an important role in biomedical diagnostics, pharmaceuticals, and biomedical, chemical, and life sciences research in the future.

SUMMARY

According to a first embodiment, an apparatus for applying a biological component to a surface includes a first substrate, means for jetting a functional agent onto the first substrate in a first pattern, means for associating a first principal substance with the first substrate, means for transferring the first principal substance from the first substrate to a second substrate in the first pattern, and means for applying a second principal substance to the second substrate. The first principal substance interacts with the second principal substance to determine a second pattern of the second principal substance associated with the second substrate.

In another aspect of the first embodiment, at least one of the first substrate and the second substrate includes at least one of a web of nitrocellulose, a membrane, a film, an electrically conductive surface, glass, a paper, a ceramic, a metal, a plastic, a tissue, a mesh, a biocompatible substrate, a gel, a rubber, a microfluidic channel, a pre-coated surface, a sterile surface, an applied principal substance, an applied functional agent, a disc, a continuous loop, a roller, a blanket roller, a hollow matrix, and a three dimensional structure.

In another aspect of the first embodiment, the surface includes at least one of a hydrophobic surface, a hydrophilic surface, a porous surface, an electrically conductive surface, a heated surface, a cooled surface, a smooth surface, a textured surface, a concave surface, a convex surface, a surface having a channel, a surface having a raised ridge, a conical surface, a cylindrical surface, a reflective surface, and a surface having a matte finish.

In another aspect of the first embodiment, the functional agent includes at least one of a chemoattractant, a chemorepellant, a multifunctional agent, an aqueous composition, a saline solution, an intracellular cell signaling chemical, an extracellular matrix protein, an antibody, a sugar, a lipid, an enzyme, a cell, a biological sample, a bodily fluid, a cell, an organelle, a peptide, a protein, a sugar, a lipid, a vesicle, a salt, a pharmaceutical compound, a nucleotide, a nucleic acid, a plasmid, a vaccine, an enzyme, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a dye, a metal, an adjuvant, a filler, a hydrophobic agent, an oxidant, a reductant, and a hydrophilic agent.

In another aspect of the first embodiment, the principal substance includes at least one of a chemoattractant, a chemorepellant, a multifunctional agent, an aqueous composition, a saline solution, an intracellular cell signaling chemical, an extracellular matrix protein, an antibody, a sugar, a lipid, an enzyme, a cell, a biological sample, a bodily fluid, a cell, an organelle, a peptide, a protein, a sugar, a lipid, a vesicle, a salt, a pharmaceutical compound, a nucleotide, a nucleic acid, a plasmid, a vaccine, an enzyme, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, glycolipid, a phospholipid, an acid, a base, a catalyst, a pigment, a dye, a metal, an adjuvant, a filler, a hydrophobic agent, and a hydrophilic agent.

In another aspect of the first embodiment, the first pattern includes at least one of a two dimensional pattern, a three dimensional pattern, a repeating pattern, a continuous pattern, an indicium, a picture, and a gradient pattern.

In another aspect of the first embodiment, the second pattern includes at least one of a two dimensional pattern, a three dimensional pattern, a repeating pattern, a continuous pattern, an indicium, a picture, and a gradient pattern.

In another aspect of the first embodiment, the first substrate and the jetting means are movable relative to one another.

In another aspect of the first embodiment, the first substrate is rotatable relative to the jetting means.

In another aspect of the first embodiment, the first and second substrates are movable relative to one another.

In another aspect of the first embodiment, the first and second substrates are rotatable relative to one another.

According to a second embodiment, a method of filtration includes the steps of jetting a first composition onto a substrate, the first composition comprising a functional agent, introducing the jetted first composition on the substrate to a second composition, the second composition comprising a target, and filtering the target from the second composition via interaction of the functional agent with the target. The interaction of the functional agent with the target removes the target from the second composition and associates the target with the first moving substrate.

In another aspect of the second embodiment, the method includes the step of transferring the target from the substrate to a further substrate.

In another aspect of the second embodiment, the method includes at least one of the steps of detecting or identifying the presence of the target on at least one of the first named substrate or the further substrate.

In another aspect of the second embodiment, the method includes the step of moving the first named substrate and the further substrate relative to one another during the transferring step.

In another aspect of the second embodiment, the method includes the step of rotating the first named substrate and the further substrate relative to one another.

In another aspect of the second embodiment, the method includes the step of moving the substrate during the jetting step.

In another aspect of the second embodiment, the step of moving the substrate during the jetting step includes the step of rotating the substrate.

In another aspect of the second embodiment, the first composition is varied over time by at least one of changing the concentration of the functional agent in the first composition or introducing a further functional agent into the first composition to regulate the interactivity of the first composition and the target.

According to a third embodiment, an apparatus for patterning a substance on a substrate includes a first substrate having a surface, means for jetting a composition including a functional agent having an affinity for a target onto the first substrate in a first pattern, means for applying a principal substance including the target to the first substrate, means for transferring the target from the first substrate to a second substrate, and means for detecting the target on the second substrate. The affinity of the first composition for the target is variable in real time.

In another aspect of the third embodiment, the apparatus further includes means for collecting the target from the second substrate.

In another aspect of the third embodiment, the apparatus further includes a cartridge including the composition.

In another aspect of the third embodiment, at least one of the first substrate and the second substrate includes at least one of a disc, a cylinder, a sphere, a belt, a band, a wire, and a chain.

In another aspect of the third embodiment, the first substrate is rotatable with respect to the jetting means.

In another aspect of the third embodiment, the first substrate is rotatable with respect to the second substrate.

According to a fourth embodiment, a method of patterning a substance on a substrate includes the steps of moving a first substrate in a plurality of cycles, during a first cycle of movement of the first substrate: (a) jetting a layer of a composition comprising a functional agent having an affinity for a target onto the first substrate, (b) applying a principal substance comprising the target to the first substrate, and (c) binding a portion of the target to the first substrate, and prior to a second cycle of movement of the first substrate subsequent to the first cycle: (a) transferring the portion of the target to a second substrate from the first substrate, and (b) cleaning the first substrate. The affinity of the functional agent for the target is optionally varied over time.

In another aspect of the fourth embodiment, the method includes the steps of moving in a plurality of cycles the second substrate, and during a third cycle of the second substrate: (a) detecting the target on the second substrate, (b) optionally collecting the target from the second substrate, and (c) cleaning the second substrate prior to a fourth cycle of movement of the second substrate subsequent to the third cycle.

In another aspect of the fourth embodiment, the affinity of the functional agent for the target is varied over time.

In another aspect of the fourth embodiment, the method includes the step of collecting the target from the second substrate.

In another aspect of the fourth embodiment, each cycle of movement of the first substrate includes rotation of the first substrate a full revolution.

In another aspect of the fourth embodiment, each cycle of movement of the second substrate includes rotation of the second substrate a full revolution.

BRIEF DESCRIPTION OF THE DRAWINGS

Features of the apparatus and methods for controlling application of a substance to a substrate will be more apparent from the following detailed description and the figures, in which;

FIGS. 10A-10C are diagrammatic views of alternative methods according to further embodiments.

DETAILED DESCRIPTION

Figure 1:
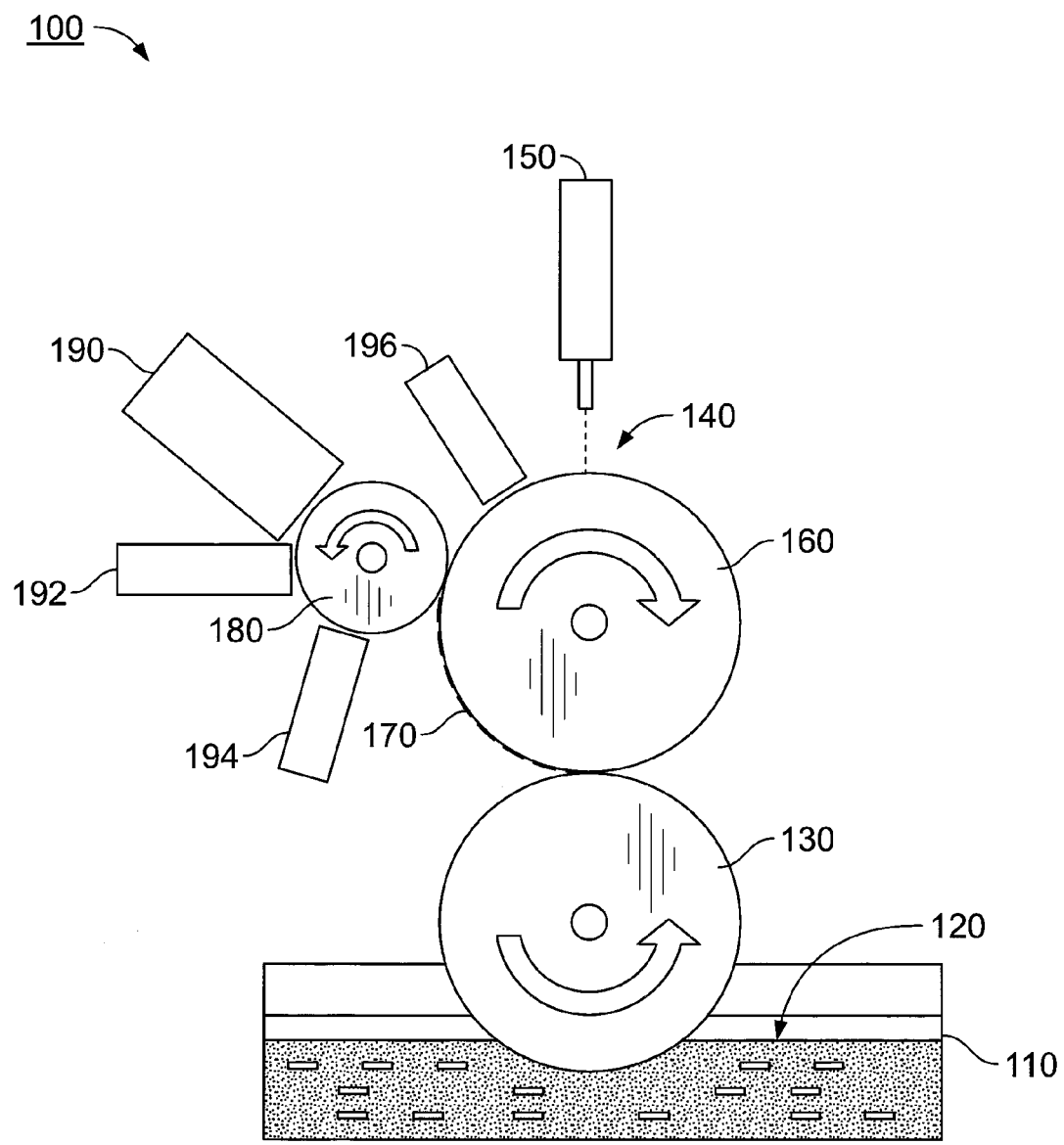
FIG. 1 is a representational depiction of a device of the present disclosure according to one embodiment.

The present disclosure introduces certain apparatuses, methods, and compositions that have been useful in the printing industry. However, recent advances in these tools permit expansion of their use into industries and for applications beyond the typical scope commonly associated with printing. For example, apparatuses and methods disclosed herein may be also relevant in other industries and other technologies including, for example, biomedical diagnostics, pharmaceuticals, and biomedical, chemical, and life sciences research, among others.

Certain underlying concepts embodied in the apparatuses, methods, and compositions disclosed herein may be related to the broader printing industry and therefore like terminology may be, in spirit, applicable and/or used interchangeably or provided for purposes of analogizing. Therefore, it is contemplated that terminology used herein may have additional meanings, for example, a pattern may be an image, an indicium, an ordered pattern, a random pattern, and the like. In another example, a web may refer to a paper web and/or a nitrocellulose substrate and/or a flexible substrate.

In one embodiment, apparatuses, methods, and compositions disclosed herein may enable medical laboratories to perform multiple analyses concomitantly on biological and chemical samples for the screening for medical conditions or broad characterization of basic attributes of such samples. Such multiplexing may reduce patient waiting, for example, in an emergency room. Further, the multifunctional possibilities of the apparatuses, methods, and compositions disclosed herein, may maximize bench space in laboratories in medical, chemical, and industrial research and therapeutic environments.

For example, an apparatus contemplated herein may dynamically isolate one or more molecules of interest or targets contained within or embodying a principal substance, and thus, in one perspective, may perform a filtering role and/or a purifying role. The apparatus may dynamically isolate the molecule by increasing overtime an affinity or attraction for the molecule by means of a functional or gating agent with which the molecule comes in contact. Viewed from another perspective, such a filtering role may enable determination of the mere presence of the target, concentration of the target, and/or stability of the target over time. Therefore, one embodiment of an apparatus contemplated herein may incorporate means to isolate one or more targets dynamically over time from a single sample, and perform subsequent steps on such one or more targets not limited to their detection, their identification, the determination of their compositions, their collection, their elimination, and their combination with other substances. For example, contemplated assays include fluorescence measurements, Förster resonance energy transfer, pH measurements, mass spectrometry, colorimetry, microscopy, viscosity, cell and tissue staining techniques, enzyme-linked assays, luminescence measurements, membrane porosity measurements, transepithelial electronic resistance, conductivity, binding propensities, reaction rates, therapeutic activity, and all other means of measurement known in the art.

It is contemplated that the apparatuses, methods, and compositions disclosed herein may have similar characteristics to other commonly used apparatuses in the medical, chemical, and industrial research and therapeutic environments. Examples of such apparatuses include high performance liquid chromatography (HPLC) systems, such as those available from Waters Corp. (Milford, Mass.), Agilent (Santa Clara, Calif.), PerkinElmer (Waltham, Mass.), Hitachi HTA Inc. (Schaumburg, Ill.), among others, are commonly used for the isolation, identification, and characterization of multitudes of compounds, including small molecules, proteins, pharmaceuticals, and the like. Further examples include flow cytometry and cell sorting systems, such as those available from Dako North America Inc. (Carpinteria, Calif.), among others, that are widely used for characterization of cell surface antigens, as well as, intracellular phenomena. Other systems that may have similar uses as those contemplated for the apparatuses, methods, and compositions disclosed herein include clinical chemistry systems, such as those available from ThermoFisher Scientific (Waltham, Mass.) and Abraxis Bioscience LLC (Los Angeles, Calif.), among others. Further, the apparatuses, methods, and compositions disclosed herein may have similar functionalities to diagnostic and/or research assays, such as, for example, enzyme-linked immunosorbent assays (ELISA), immunoblots, Southern blots, Northern blots, Western Blots, polymerase chain reaction, and transcriptional profiling via nucleic acid arrays, and those techniques that may be used to identify proteins, protein-nucleic acid interactions, and nucleic acid-nucleic acid interactions, as is known in the art. Additional functionalities that perform the same or similar roles of apparatuses, assays, and kits useful in the medical, chemical, and industrial research and therapeutic environments are further contemplated herein.

In one embodiment, apparatuses for applying a component to a surface may include a moving first substrate, means for jetting a functional agent onto the moving first substrate in a first pattern, means for associating a first principal substance with the moving first substrate, means for transferring the first principal substance from the moving substrate to a moving second substrate in the first pattern, and means for applying a second principal substance to the moving second substrate. The first principal substance may interact with the second principal substance to determine a second pattern of the second principal substance associated with the moving second substrate. In another embodiment, the substrate may include at least one of a web of nitrocellulose, a membrane, a film, an electrically conductive surface, glass, a paper, a ceramic, a metal, a plastic, a tissue, a mesh, a biocompatible substrate, a gel, a rubber, a microfluidic channel, a pre-coated surface, a sterile surface, an applied principal substance, an applied functional agent, a disc, a continuous loop, a roller, a blanket roller, a hollow matrix, and a three dimensional structure. In a further embodiment, the surface may include at least one of a hydrophobic surface, a hydrophilic surface, a porous surface, an electrically conductive surface, a heated surface, a cooled surface, a smooth surface, a textured surface, a concave surface, a convex surface, a surface having a channel, a surface having a raised ridge, a conical surface, a cylindrical surface, a reflective surface, and a surface having a matte finish.

In yet another embodiment, the functional agent may include at least one of a chemoattractant, a chemorepellant, a multifunctional agent, an aqueous composition, a non-aqueous composition, a saline solution, an intracellular cell signaling chemical, an extracellular matrix protein, an antibody, a sugar, a lipid, an enzyme, a cell, a biological sample, a bodily fluid, a cell, an organelle, a peptide, a protein, a sugar, a lipid, a vesicle, a salt, a pharmaceutical compound, a nucleotide, a nucleic acid, a plasmid, a vaccine, an enzyme, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a dye, a metal, an adjuvant, a filler, a hydrophobic agent, an oxidant, a reductant, and a hydrophilic agent. Further, the principal substance may include at least one of a chemoattractant, a chemorepellant, a multifunctional agent, an aqueous composition, a non-aqueous composition, a saline solution, an intracellular cell signaling chemical, an extracellular matrix protein, an antibody, a sugar, a lipid, an enzyme, a cell, a biological sample, a bodily fluid, a cell, an organelle, a peptide, a protein, a sugar, a lipid, a vesicle, a salt, a pharmaceutical compound, a nucleotide, a nucleic acid, a plasmid, a vaccine, an enzyme, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a dye, a metal, an adjuvant, a filler, a hydrophobic agent, and a hydrophilic agent. In a still further embodiment, at least one of the first pattern and the second pattern includes at least one of a two dimensional pattern, a three dimensional pattern, a repeating pattern, a continuous pattern, an indicium, a picture, and a gradient pattern.

In accordance with another embodiment, a method of filtration may include jetting a first composition onto a first rotating substrate, the first composition including a functional agent. The method may further include introducing the jetted first composition on the first rotating substrate to a second composition, the second composition including a target. Further, the method may include filtering the target from the second composition via interaction of the functional agent with the target. The interaction of the functional agent with the target may associate the target with the first rotating substrate. In a first additional embodiment, the method may further include transferring the target from the first rotating substrate to a second substrate. In a second additional embodiment, the method may further include detecting the presence of the target on at least one of the first rotating substrate or the second substrate. In a third additional embodiment, the method may further include identifying the target on at least one of the first rotating substrate or the second substrate. In another additional embodiment, the functional agent may be varied overtime to regulate the interactivity of the functional agent and the target.

According to another embodiment, an apparatus for patterning a substance on a substrate may include a first rotating substrate having a surface, means for jetting a composition including a functional agent having an affinity for a target onto the first rotating substrate in a first pattern, means for applying a principal substance including the target to the first rotating substrate, means for transferring the target from the first rotating substrate to a second substrate, and means for detecting the target on the second substrate. The affinity for the functional agent for the target may be variable in real time. In another embodiment, the apparatus may further include means for collecting the target from the second substrate. In a further embodiment, the apparatus may further include a cartridge including the composition including the functional agent. In a still further aspect, at least one of the first rotating substrate and the second substrate may include at least one of a disc, a cylinder, a sphere, a belt, a band, a wire, and a chain.

According to a further embodiment, a method of patterning a substance on a substrate may include rotating a first substrate, during a revolution of the first substrate: jetting a layer of a composition including a functional agent having an affinity for a target onto the first substrate, applying a principal substance including the target to the first substrate, and binding a portion of the target to the first substrate, and prior to a subsequent revolution of the first substrate: transferring a portion of the target to a second substrate from the first substrate, and removing the layer of the composition from the first substrate. The affinity of the functional agent for the target may be optionally varied over time. In another embodiment, the method may further include rotating the second substrate and during a revolution of the second substrate: detecting the target on the second substrate, and optionally collecting the target from the second substrate. The method may further include, prior to a subsequent revolution of the second substrate, cleaning the second substrate. In a further embodiment, the affinity of the functional agent for the target may be varied over time. In an additional embodiment, the target may be collected from the second substrate.

Illustratively, FIG. 1 depicts an apparatus 100 contemplated herein that may incorporate one or more of the characteristics, functions, and/or components of the apparatuses in the medical, chemical, and industrial research and therapeutic environments mentioned above. The apparatus 100 includes a sample reservoir 110 containing a principal substance 120. The principal substance 120 may be applied to a first substrate 130 that carries a portion of the principal substance on a surface thereof to come into contact with a functional agent 140 which has been patterned by a jetting head 150 upon second substrate 160. One or more targets within the principal substance 120 are selected by the functional agent 140 to form complexes 170 on the second substrate 160, which may then be transferred to a third substrate 180 for additional processing, such as detection, identification, characterization, combination with additional materials, or other analysis of the one or more targets by detector/analyzer 190. Targets of interest may be collected using collector/analyzer 192 for further processing, analysis, and the like. A first cleaning component 194 may be used to clean and/or sterilize the third substrate 180. Similarly, a second cleaning component 196 may be used to clean and/or sterilize the second substrate 160. Likewise, if desired, a cleaning component may be associated with the first substrate, for example, to prevent potential contamination of the reservoir 110.

The components of FIG. 1 may be modified, multiplied, and/or deleted as necessary to achieve an apparatus having the desired characteristics of an end-user. For example, the first substrate 130 may be removed resulting in both the principal substance 120 and functional agent 140 being introduced to the same substrate 160. In such case, the substrate 160 may contact the principal substance 120 similar to the manner shown in FIG. 1, or the principal substance may be applied using a jet head or some other device. In the first scenario, only the one or more targets for which the functional agent has an affinity would be drawn from the reservoir, in the second scenario, the substrate 160 may repel the principal substance unless associated with the functional agent.

In another embodiment, the apparatuses, methods, and compositions disclosed herein may be used to combine principal substances on a substrate for analytical purposes, cell science studies, tissue building, organ building, pharmaceutical manufacturing, such as the formation of a dose form, among others. In this embodiment, a candidate apparatus may selectively pattern a principal substance on a non-patterned substrate or on a previously patterned substrate to accumulate similar or dissimilar principal substances in a predetermined pattern. Possible predetermined patterns include, for example, a two dimensional pattern, a three dimensional pattern, a gradient pattern, a repeating pattern, a discrete pattern that could be the basis of a dosage form, such as a pill, or a portion of a dosage form that could be combined with other ingredients in a subsequent step or concomitantly to form a dosage form, a continuous pattern, an indicium, and a picture.

Figure 2:
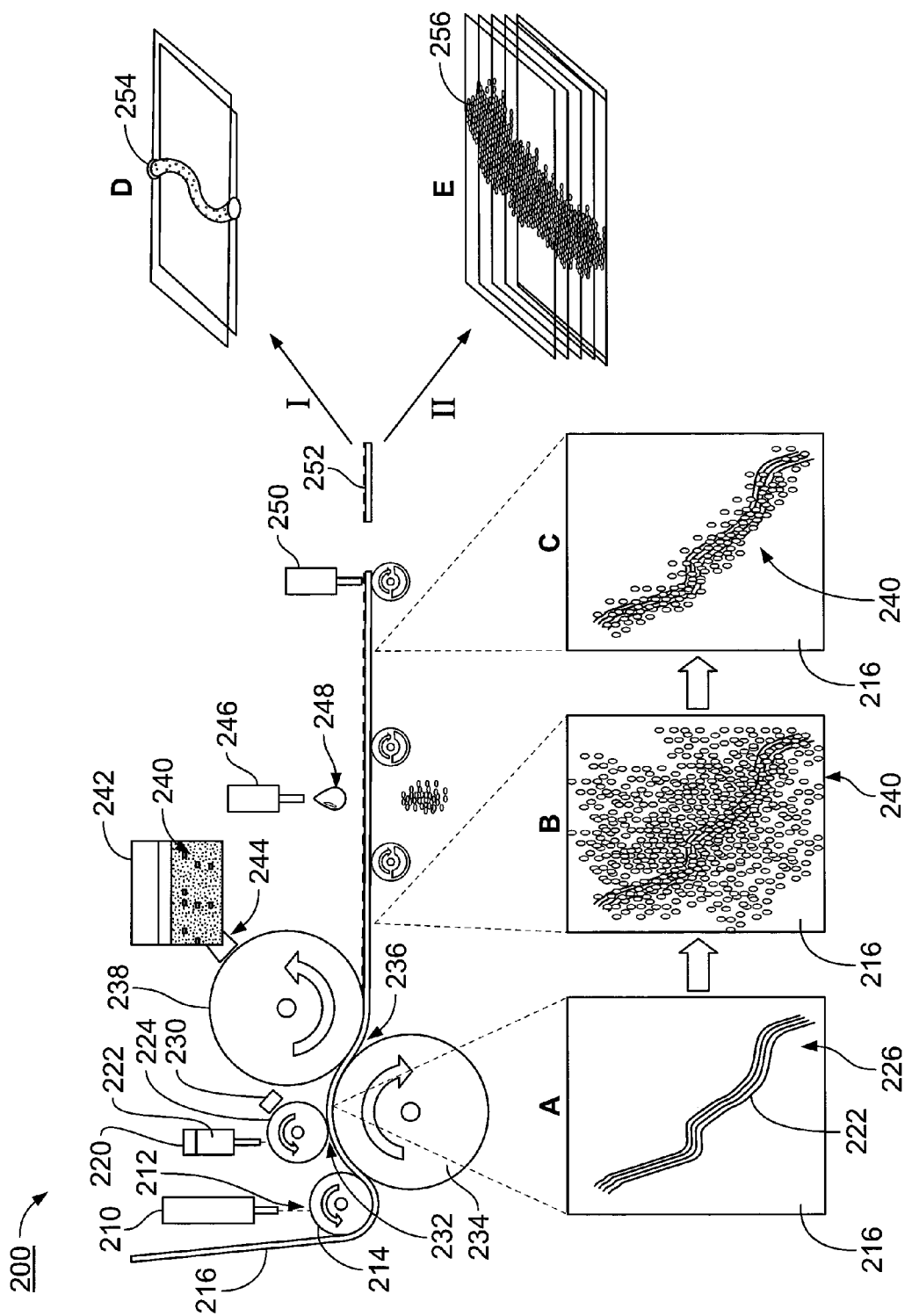
FIG. 2 is a representational depiction of a device of the present disclosure according to another embodiment.

Illustratively, FIG. 2 depicts an apparatus 200 that may be used for analytical purposes, cell science studies, tissue building, organ building, pharmaceutical manufacturing, such as the formation of a dose form, among other uses. The apparatus 200 includes a jetting head 210 that may pattern a functional agent 212 onto a first substrate 214, which transfers the functional agent to another substrate, which in this case is described for ease of explanation as "print medium" 216. A first reservoir 220 containing a first principal substance 222 may apply the first principal substance to a second substrate 224, which introduces the first principal substance 222 to the functional agent 212 patterned on the print medium 216. Interaction of the functional agent 212 with the first principal substance 222 may allow the first principal substance to become associated with the print medium 216. For example, breakout panel A shows an example of how a pattern 226 of first principal substance 222 may appear after association with the patterned functional agent on the print medium 216. Here, only the first principal substance 222 that was predisposed to interacting with the first functional agent 212 was transferred from the second substrate 224 to the print medium 216. The remaining principal substance on the second substrate 224 may be removed from the second substrate via a cleaning component 230. The cleaning component 230 may remove the first principal substance 222, which may then be recycled back into reservoir 220, and further clean and/or sterilize the second substrate 224 in preparation for subsequent use.

The first principal substance 222 is introduced to the print medium 216 at a first nip 232 between the second substrate 224 and an impression cylinder 234. At a second nip 236 between a third substrate 238 and the impression cylinder 234, a second principal substance 240 is introduced to the print medium 216, which may appear as in break out panel B. The second principal substance 240 may selectively interact with the first principal substance 222 on the print medium 216, such that the first principal substance serves as a point of attachment for targets within the second principal substance. For example, the first principal substance 222 may be one or more extracellular matrix proteins, growth factors, antibiotics, and the like, and the second principal substance 240 may be a cell suspension, biological sample, and the like. The second principal substance 240 may be stored within a second reservoir 242 and also may be applied to the third substrate 238 via an applicator 244, such as a jetting head, a robotic pipettor, a cell sorter, or other suitable device.

The print medium 216 may be washed after application of the second principal substance 240 by a cleaning device 246, which may introduce a cleaning agent 248 to the print medium via spraying, jetting, dipping, pouring, misting, and/or vacuum. The cleaning agent 248 may include a physiological solution, such as a salt-containing solution, or other suitable composition. The cleaning agent may optionally incorporate additional compounds, including biocides that may select against (e.g., remove) cells attached to the print medium 216 but that are not associated with the patterned functional agent. Positive selection of the second principal substance 240 by the first principal substance 222 may be evidenced post-washing of the print medium 216, as seen in break out panel C. In break out panel C, the second principal substance 240 has been retained on the print medium 216 as a result of interaction with the first principal substance.

A further processing component 250 may take on the form of a cutter, detector, fluorescent light emitter, laser, microscope, or any other desired component. In one scenario depicted along arrow I and in break out panel D, two sheets 252 or units of print medium with patterned principal substances may be stacked and cultivated to form a tubular tissue 254, such as a blood vessel. In a second scenario depicted along arrow II and in break out panel E, multiple sheets or units may be stacked to form complex and/or large tissues and/or organs 256 having gradients of cellular complexity mimicked via patterning.

It is contemplated herein, that a substrate used for such applications may further contain nutrient factors and other chemicals to help support, select cell subtypes, and direct cell growth and/or migration of attached cells, have a three dimensional matrix characteristic to promote three dimensional cell structures, as well as being degradable over time to allow cells from stacked sheets to interact in an unimpeded manner after a period of time. It is further contemplated that analytical and/or diagnostic reagents that may stain the cells for later viewing via microscopy, treat the cells for subsequent analysis, and the like, may be included in some or all of the compositions described herein. Reagents may vary according to the nature of the functional agent, principal substance, substrate, print medium, and/or desired end result of the user. Additional non-exhaustive variations in the functional agents, substrates, principal substances, and additives contemplated for use in the apparatuses and methods described herein are further expanded upon below.

Further, it is contemplated that the apparatuses disclosed herein may include discrete environmentally controlled regions that may differ from one another in terms of temperature, sterility, pressure, gas content, humidity, luminescence, and the like. Any portion of a device contemplated herein may be heated or cooled to temperatures ranging from about 273° C. to greater than about 250° C., or from −80° C. to about 100° C., or from about −20° C. to about 96° C., or from about 0° C. to about 80° C., or from about 4° C. to about 72° C., or about 60° C., or about 55° C., or about 50° C., or about 45° C., or about 42° C., or about 37° C., or about 25° C. For example, the apparatus 200 in FIG. 2 may hold the jetting head 210 at 4° C. and the first substrate 214 at 4° C., and the impression cylinder 234, the second reservoir 242, applicator 244, third substrate 238, and region downstream of nip 236 at 37° C. Further, impression cylinder 234 may be held at 4° C. at nip 232 and warmed to 37° C. by the time it reaches nip 236. Additional environmental manipulations are contemplated herein.

Further, the additional processing steps indicated downstream of break out panel C may be performed and carried out within the apparatus 200 or without the apparatus 200 in detached incubators (not shown).

Figure 3:
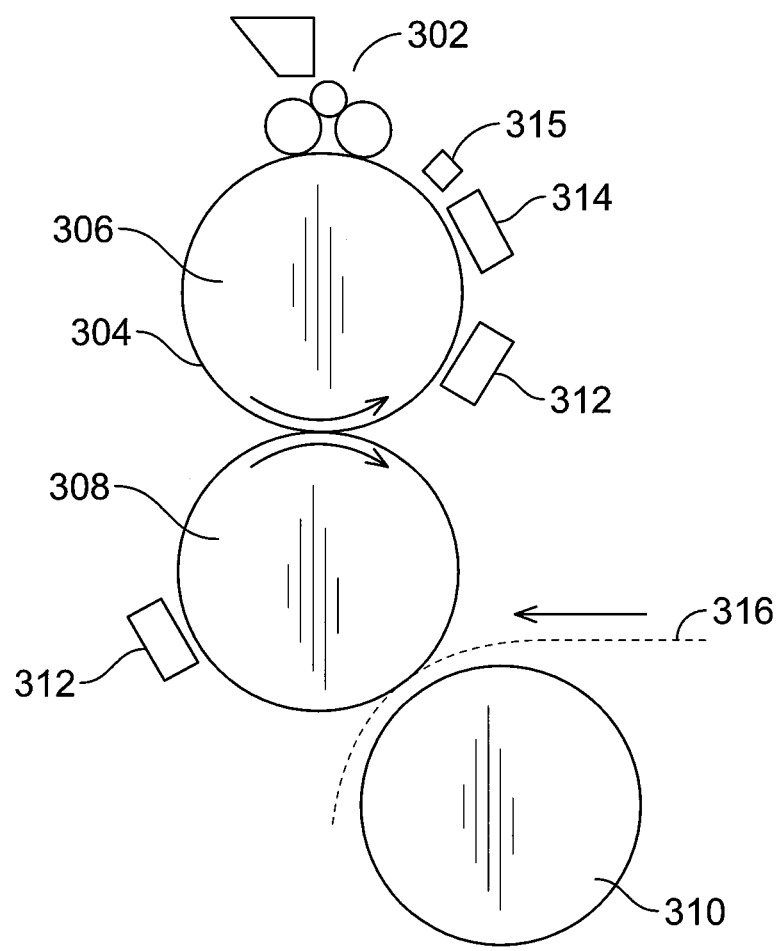
FIG. 3 is a side view of an illustrative embodiment of an apparatus for controlling application of a substance to a substrate.

Another apparatus that may be used for patterning one or more principal substances on a substrate is seen in FIG. 3. FIG. 3 illustrates a contemplated apparatus 300, which may include inking system 302, which may apply a principal substance, a first substrate, such as a plate 304, a plate cylinder 306, a second substrate, such as a blanket cylinder 308, and an impression cylinder 310. Plate 304 may be partially or entirely hydrophilic (for example, a standard aluminum lithographic plate).

Jet systems useful herein may utilize aqueous compositions, non-aqueous compositions, and combinations thereof. Examples describing one system should be understood to be representative only and not exclusive of other possibilities disclosed herein. Such unilateral discussion is for the sake of clarity.

An aqueous jet system 314 may contain a series of jet cartridges. The aqueous jet system 314 may be used to emit an aqueous solution containing one or more functional agents, for example, surfactants on a hydrophilic plate. Such surfactants may contain a hydrophilic group at one end and a hydrophobic group at the other end of each molecule. Adding one or more surfactants to the aqueous solution may improve the surface tension properties of the aqueous solution. The aqueous solution may be ejected through traditional jet nozzles (for example, heads). The aqueous jet system 314 may also support variable patterning speeds and output resolutions.

In one embodiment, a pattern controller may receive pattern data from a data system. The pattern data may represent the pattern to be printed. The pattern data may include variable pattern data, fixed pattern data, and any combination of variable, semi-fixed, and fixed pattern data. The pattern data may be stored as binary data, bitmap data, page description code, or a combination of binary data, bitmap data, and page description code, or is any other suitable form. For example, a page description language (PDL), such as PostScript or Printer Command Language (PCL), may be used to define and interpret pattern data in some embodiments. A data system may then electronically control aqueous jet system 314 to print a pattern in aqueous solution represented by some or all of the different types of pattern data (or any portion thereof) onto plate cylinder 306.

In another embodiment, a vacuum source or heat source 315 may be positioned next to or near aqueous jet system 314. In some embodiments, vacuum source or heat source 315 may be integrated with aqueous jet system 314. The vacuum source or heat source may be used to reduce the size of the individual drops of aqueous solution placed by aqueous jet system 314 by blowing, drying, and/or heating the aqueous solution after it is printed onto plate 304 or plate cylinder 306. Alternatively, any process parameter, including ambient conditions, such as humidity and temperature levels, could be manipulated that could affect drop formation and other surface phenomena on a substrate contemplated in this disclosure. For example, the ability to control drop size of the aqueous solution may improve the quality of the printed pattern.

As plate cylinder 306 completes a revolution, after passing the pattern to blanket cylinder 308, it passes through cleaning system 312, which may remove residual principal substance and/or aqueous solution residue so that plate cylinder 306 may be re-patterned by aqueous jet system 314 during the next revolution (or after a certain number of revolutions). Cleaning system 312 may comprise a rotary brush, a roller having a cleaning solution, a belt, a cleaning web treated with a cleaning solution, an apparatus for delivering heat and/or air, an electrostatic apparatus, or any other suitable means of removing principal substance, aqueous solution residue, or both, from plate cylinder 306. In some embodiments, blanket cylinder 308 may also have a cleaning system similar to cleaning system 315 to clean any residual material from blanket cylinder 308 after the pattern has been transferred to the final substrate 316.

In another embodiment, plate cylinder 306 may have all of the static data for a particular print job etched onto plate 304 by traditional lithographic techniques. Aqueous jet system 314 may then be used to pattern only variable portions of the job represented by the variable or semi-fixed pattern data on specified portions of plate 304. Such an arrangement may be useful, for example, for creating personalized diagnostic tests that share basic informational formatting, such as directions for use, and may further include a biological or chemical reagent personalized to a patient (including an individual's test sample) or generic for any end user.

In other embodiments, plate 304 may not be used. Instead, the surface of plate cylinder 306 may be treated, processed, or milled to receive the aqueous solution from aqueous jet system 314. Additionally, plate cylinder 306 may be treated, processed, or milled to contain the static data and be receptive to the aqueous solution to incorporate variable data (for example, individual patient samples or separate assay samples). In these and any other embodiments herein, blanket cylinder 308 may be eliminated entirely, if desired, by transferring the pattern directly to a substrate, such as web 316.

In another embodiment, one or more of plate 304, plate cylinder 306, and blanket cylinder 308 may be customized or designed to work with various properties of aqueous jet system 314 or the aqueous solution. For example, one or more of these plates and cylinders may be specially processed or milled to only accept solution ejected by print heads of a particular resolution or dot size. The plates and cylinders may also be specially processed to accept certain types of aqueous solutions and reject others. For example, the plates and cylinders may accept solutions of a certain volume, specific gravity, viscosity, or any other desired property, while rejecting solutions outside the desired parameters. This may prevent, for example, foreign agent contamination and allow for one aqueous solution to be used in the patterning process and another aqueous solution (with different physical properties) to be used in the cleaning process. Further, discriminating patterning surfaces may increase target resolution when only a portion of a principal substance is desired to be retained on a substrate. In this way, non-target substances may be excluded more readily from the substrate resulting in a more pure extraction of target substance.

Figure 4:
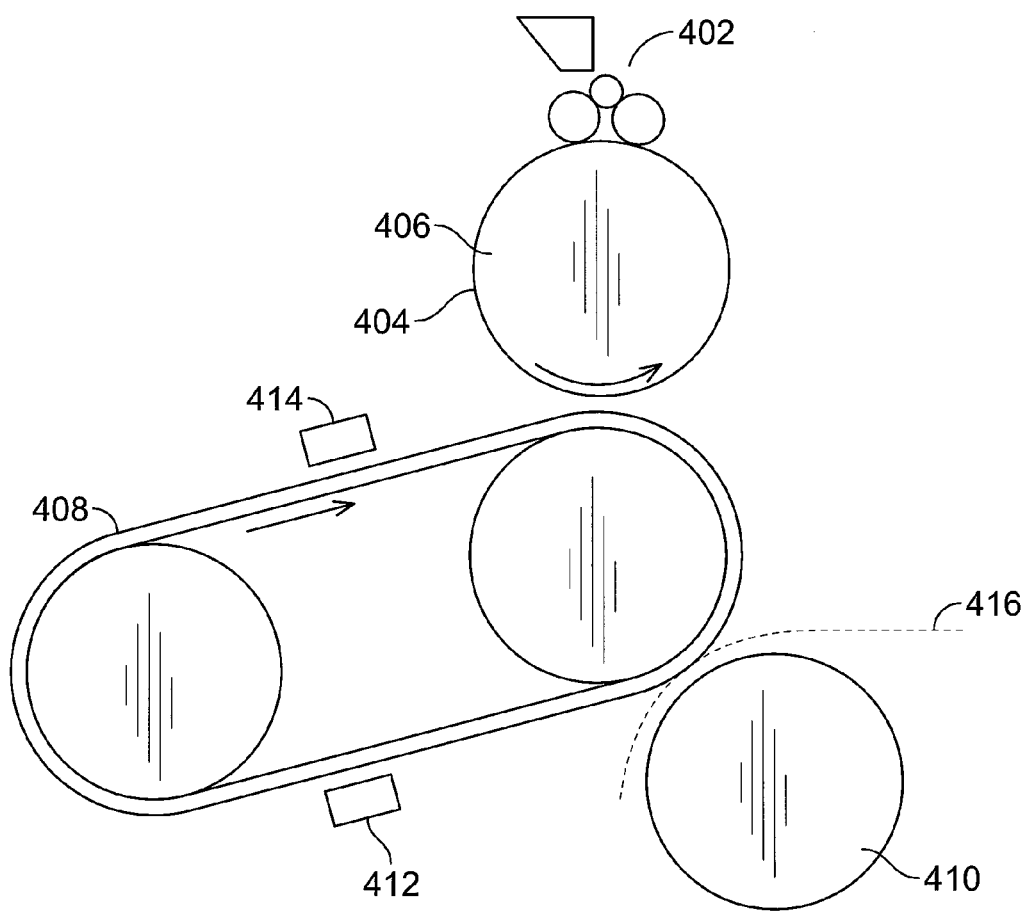
FIG. 4 is a side view of another embodiment of an apparatus for controlling application of a substance to a substrate.
Figure 5:
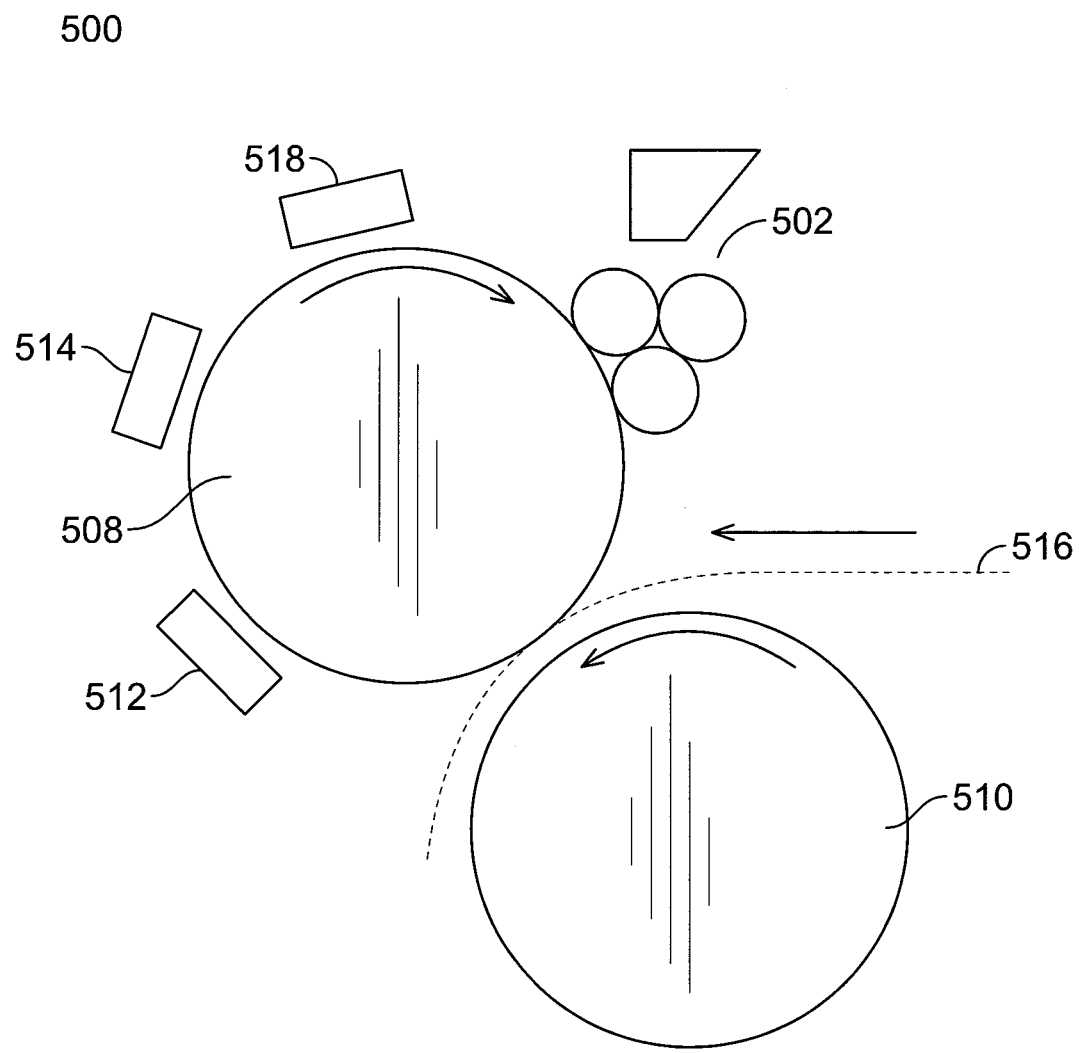
FIG. 5 is a side view of a further embodiment of an apparatus for controlling application of a substance to a substrate.

The aqueous jet system and cleaning system may be mounted in other arrangements as well. As shown in the example of FIG. 4, patterning deck 400 allows for more flexibility in the placement of aqueous jet system 414 and cleaning system 412. In the example of FIG. 5, the blanket cylinder may be replaced with endless belt 408 or other revolving and/or renewing substrate. In some embodiments, the length of endless belt 408 may be adjustable to accommodate various additional systems or more convenient placement of aqueous jet system 414 and cleaning system 412. Aqueous jet system 414 and cleaning system 412 may be mounted at any suitable location along endless belt 408. As described above with regard to FIGS. 4 and 5, patterning deck 400 may also include inking system 402, plate cylinder 406, plate 404, and web 416 or other substrate between endless belt 408 and impression cylinder 410. Endless belt 408 may be variably patterned with an aqueous solution as described above with regard to blanket cylinder 308 of FIG. 4, such that principal substance is only transferred to certain portions of endless belt 408 for transfer to web 416.

In another embodiment, shown in FIG. 5, aqueous jet system 514 may be used to print an aqueous solution containing a functional agent, such as a surfactant including a block copolymer onto patterning cylinder 508. One example of such a surfactant is BASF's Pluronic® F-127 surfactant. These surfactants may be used to vary the surface properties of patterning cylinder 508 between hydrophilic and hydrophobic.

The aqueous jet system 514 may be used to print a pattern onto patterning cylinder 508. Then, a heat source, for example, dryer 518 or any other suitable means of evaporating the water, may be used to dry the aqueous solution. This will leave the block copolymer bonded to patterning cylinder 508 at the location at which it was printed by aqueous jet system 514. The block copolymer may be chosen such that one end bonds with surface material of the patterning cylinder while the other end is hydrophobic. If a naturally hydrophilic patterning cylinder is used, then the patterning cylinder will be hydrophobic everywhere that aqueous jet system 514 printed the block copolymer, and hydrophilic everywhere else. The patterning cylinder may now be used in a process similar to lithography. For example, a principal substance may be constantly applied to patterning cylinder 508 by inking system 502. The pattern may then be transferred to the print medium (for example, web 516 between patterning cylinder 508 and impression cylinder 510).

The embodiment of FIG. 5 may also include cleaning system 512. The cleaning system may only selectively engage patterning cylinder 508. Because the block copolymer surfactant has been physically bonded to patterning cylinder 508, it may not be removable by mechanical means. In other words, the patterning cylinder may be used repeatedly, as if it were a standard lithographic plate. When the data system controlling the press determines that information needs to be varied, cleaning system 512 may selectively release some of the block copolymers. For example, a chemical that negates the bond between the block copolymer and the patterning cylinder could be used to remove the block copolymer in select locations or as varies due to differential chemical nature of the one or more aqueous solutions present on the substrate. Those of ordinary skill in the art will recognize that any suitable means of releasing the bond between the block copolymer and patterning cylinder 508 may be employed to selectively release the block copolymer. For example, a reducing agent may be used to negate the bond between the block copolymer and patterning cylinder 508.

In yet another alternative of the FIG. 5 embodiment, charged molecules, such as block copolymer surfactant molecules, may be employed so that the bond between patterning cylinder 508 and the charged molecules can be electronically controlled. In other words, aqueous jet system 514 may be used to place charged surfactants at the desired location. The charged properties of the surfactant molecules may be what permit their physical bond to patterning cylinder 508. Thus, removing them may require selectively applying a neutralizing charge from cleaning system 512.

Alternatively or in addition, patterning cylinder 508 may have a charged surface that may be controllable to change the charged property of a particular point on the patterning cylinder at a particular time. Points on patterning cylinder 508 may be toggled between positively and negatively charged to attract and repel the surfactants at the appropriate time in the patterning process.

Figure 6:
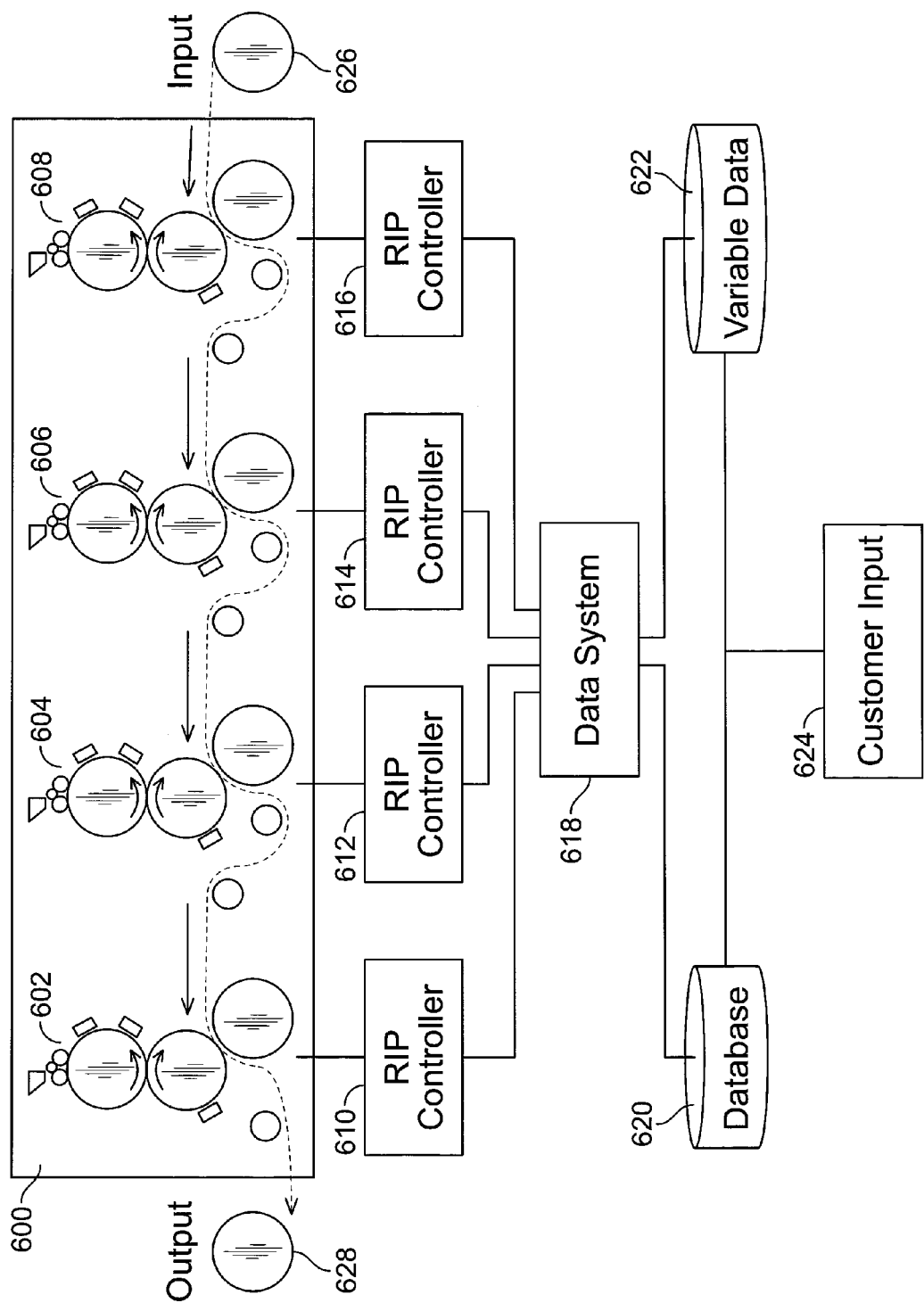
FIG. 6 is a side view of a still another embodiment of an apparatus for controlling application of a substance to a substrate.

Multiple patterning decks like those shown herein may be mounted in a series in a single apparatus 600, such as is shown in FIG. 6. This may be done, for example, to allow for multiple layer patterning, similar to four color printing, which uses four decks each of which is responsible for printing in one of cyan, magenta, yellow, or black. In another embodiment, multiple decks may be used to form three dimensional patterns of principal substances and/or target substances with functional agents. Each of the decks 602, 604, 606, and 608 may be controlled by its own raster pattern processor ("RPP") or controller, such as controllers 610, 612, 614, and 616. Controllers 610, 612, 614, and 616 may be implemented in hardware and/or software, for example, as part of a printer driver. If desired, the controllers 610-616 may be replaced by fewer than or more than four RPP's. For example, a single RPP may electronically process data and control the decks 602-608.

The entire apparatus may be managed by a single data system, such as data system 618, that controls RPP controllers 610, 612, 614, and 616, which in turn control decks 602, 604, 606, and 608, respectively. Data system 618 may be provided with customer input 624 via database 620 and variable data source 622. Database 620 may include pattern data and other information.

In some embodiments, database 620 contains all the layout information and static pattern information for the pattern to be printed, while variable data source 622 contains all the variable data. In one example contemplating individualized considerations, customer input 624 may provide customer data (for example, layout and content preferences) to database 620. Variable data source 622 may store personalized text (for example, the customer's name and location) and graphics. Data system 618 may then access both database 620 and variable data source 622 in order to print a job and/or process a sample. Database 620 and variable data source 622 may include any suitable storage device or storage mechanisms (for example, hard drives, optical drives, RAM, ROM, and hybrid types of memory). Apparatus 600 may be fed by roll or sheet input 626. Output 628 of the press may also be in the roll or sheet format. Additionally, output 628 of press 600 may be fully-bound or may be prepared for optional post-processing.

One or more of the aqueous jet systems, cleaning systems, stripping systems, and vacuum or heating systems described herein may be electronically controlled via data system 618. For example, in a possible usage scenario, data system 618 may access raster pattern data (or any other type of pattern data, including, for example, bitmap data, vector graphics pattern data, or any combination thereof) from database 620 and/or variable data source 622. In some embodiments, the pattern data may be stored in page description code, such as PostScript, PCL, or any other PDL code. The page description code may represent the pattern data in a higher level than an actual output bitmap or output raster pattern. Regardless of how the pattern data are stored, data system 618 may cause the aqueous jet system disclosed herein to print an pattern representing the pattern data (or any portion thereof) in aqueous solution to a plate, plate cylinder, or other substrate. In some embodiments, as described above, only the data represented by the variable pattern data may be printed in aqueous solution on the plate or plate cylinder.

Controlling the entire press from a single data system, such as data system 618, may enable a user to take advantage of form lag techniques. Form lag is a printing industry phenomenon that relates to the timing of multiple variable printing devices acting on the same substrate. Certain materials may need to be printed by one deck while another portion of materials may need to be printed by another deck on the same substrate. In this respect, it may be beneficial to delay the transmission of data to the latter deck, because the printed pattern may pass through several intermediary decks before reaching the latter deck. By efficiently managing form lag, pattern resolution and placement may be improved.

Figure 7:
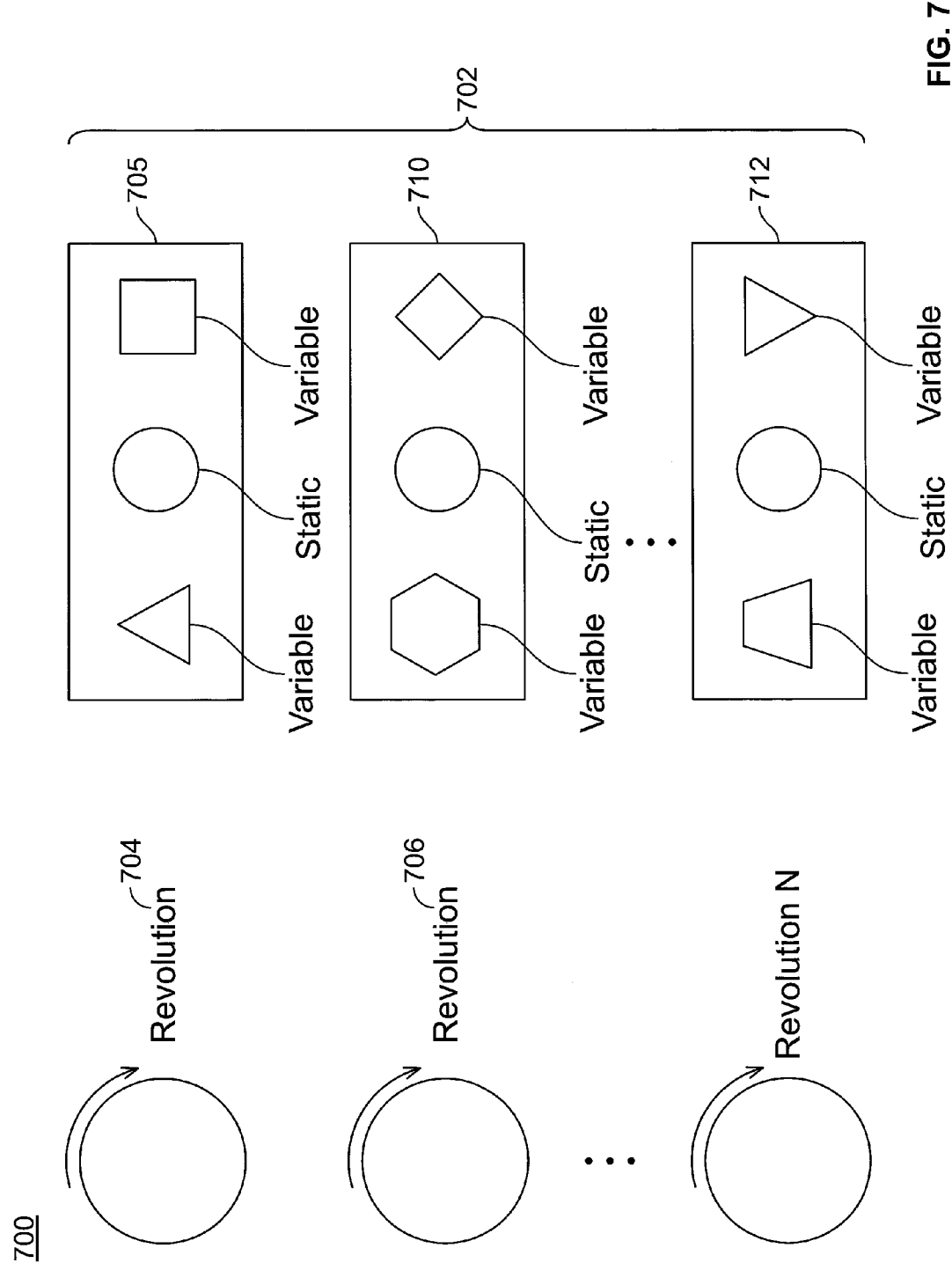
FIG. 7 is an illustration of a possible sequence of output.

FIG. 7 shows illustrative output 702 from a press in accordance with the present disclosure. Each revolution 704, 706, . . . , N of the plate or blanket cylinder may produce, for example, a pattern containing one static pattern and two variable patterns as shown in patterns 705, 710, and 712. Any combination of static and variable information may be produced by such a press. Furthermore, one revolution of the cylinder does not need to match one iteration of output. Depending on the cylinder size, multiple pages may be printed by the revolution of some cylinders, while the revolution of other cylinders may only produce a portion of an output page or other measure of substrate units.

The aqueous jet units contemplated for use herein may be known print cartridge units such as those manufactured by HP, Lexmark, Spectra, Canon, etc, or may be specially fabricated units designed to meet the specification of a given apparatus as contemplated herein. Each jet unit may comprise any number of small holes for emitting the aqueous solution. Jet heads having multiple channels may be used, wherein each channel is normally intended to apply a particular substance to a substrate. In such a case, the jet head can be used to supply functional agent(s) via each channel (either at the same times or at different times during a production sequence) so that higher resolution, higher run speeds, or other desirable results may be achieved.

Jet head(s) or cartridge(s) may be positioned depending on the desired functionality thereof in a number of positions relative to other components of the apparatus. As described previously, one or more jet cartridges may be positioned to apply a functional agent ejected therefrom onto a substrate, such as a plate cylinder. Further, one or more jet cartridges may apply a cleaning solution to one or more pattern areas of the plate cylinders or to a blanket cylinder. The jet cartridge(s) may further be positioned relative to each of the components, for example, above or below each component, or ahead of or behind each component relative to the path that the substrate relative to the print heads.

Any of the systems described herein may be modified to allow formation of different drop sizes of functional agent. For example, jet heads manufactured by HP may be used to obtain drop sizes on the order of 14 picoliters (pl) up to 1200 dots per inch (dpi) resolution whereas jet heads manufactured by Xaar are capable of ejecting 3 pl drops at 360 dpi but may also eject 6 pl, 9 pl, and 12 pl drops. Disparate jet head technologies, such as both HP and Spectra, may be used in a single system to produce a wider range of drop sizes. The resolution of the resulting patterned areas can be controlled through appropriate selection of the jet head(s) used to apply the functional agent. In general, a larger drop size is more susceptible to forced wetting of areas to be patterned. Forced wetting can result from merging of adjacent jetted drops when the pattern is transferred between surfaces (such as in the nip area between a plate and blanket) and, on the one hand, can cause a decrease in pattern quality due to a reduction in print density. However, on the other hand, such forced wetting between adjacent jetted drops that vary in concentration of a functional agent, may serve to form patterned micro-gradients on a substrate that may be useful for varying the affinity of the pattern gradient for a principal substance over variably sized distances.

Figure 8:
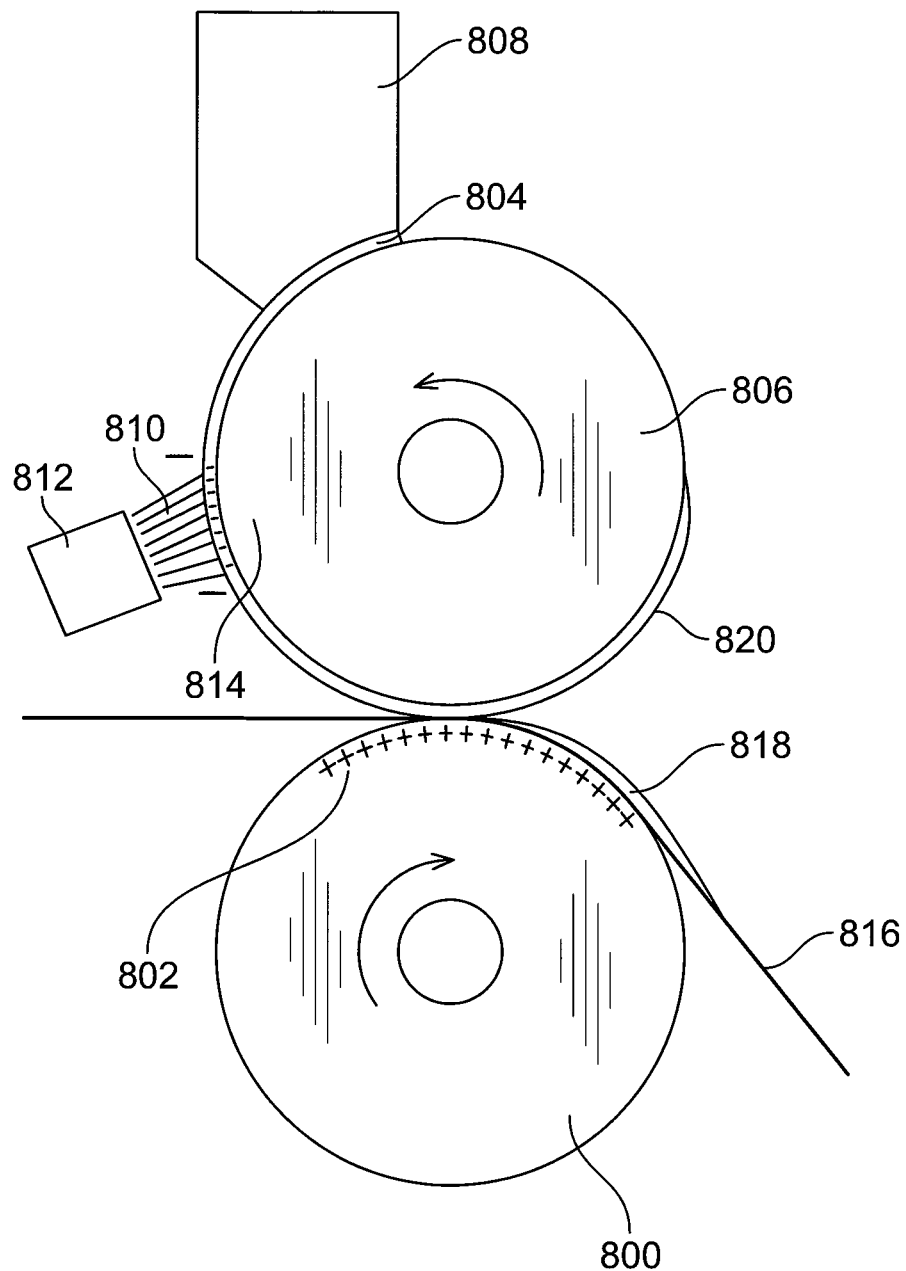
FIGS. 8-9 are side views of additional embodiments of an apparatus for controlling application of a substance to a substrate.

In another embodiment, an electrostatic charge may be used to aid in the application of the principal substance and/or functional agent to the substrate. For example, as shown in FIG. 8, an impression cylinder 800 may have an electrostatic charge 802 applied thereto. The electrostatic charge 802 may be positive or negative and may be applied to a portion of the impression cylinder 800 or to the entirety thereof. The principal substance 804 may be uniformly applied to a substrate, such as a plate or a blanket cylinder 806 by a principal substance train 808. An electrostatically charged functional agent having a charge opposite that applied to the impression cylinder 800, for example, a negatively charged aqueous solution 810, may be selectively sprayed from an jet head 812 over a pattern area 814 on the blanket cylinder 806. The aqueous solution 810 is formulated to bind to the principal substance 804 with a binding strength greater than that between the principal substance and the blanket cylinder 806. A substrate, for example, a membrane 816, may be guided between the impression cylinder 800 and the blanket cylinder 806. Each of the impression cylinder 800 and the blanket cylinder 806 may rotate such that respective surfaces thereof may move in a common direction proximate to the membrane 816 guided therebetween. As the blanket cylinder 806 rotates, the negatively charged aqueous solution 810 that covers the pattern area 814 may be electrostatically attracted to the impression cylinder 800. The negatively charged aqueous solution 810 may separate from the blanket cylinder 806 pulling the principal substance 804 in the pattern area 814 on the blanket cylinder onto the membrane 816 to form a second pattern 818. Residual principal substance 820 that is not covered by the negatively charged aqueous solution 810 remains bound to the blanket cylinder 806. Further rotation of the blanket cylinder 806 allows the principal substance train 808 to uniformly replenish the principal substance 804 carried thereon. The impression cylinder 800 may remain charged throughout the process just described or may be charged and discharged to correspond with the proximity of the pattern area 814 thereto.

Figure 9:
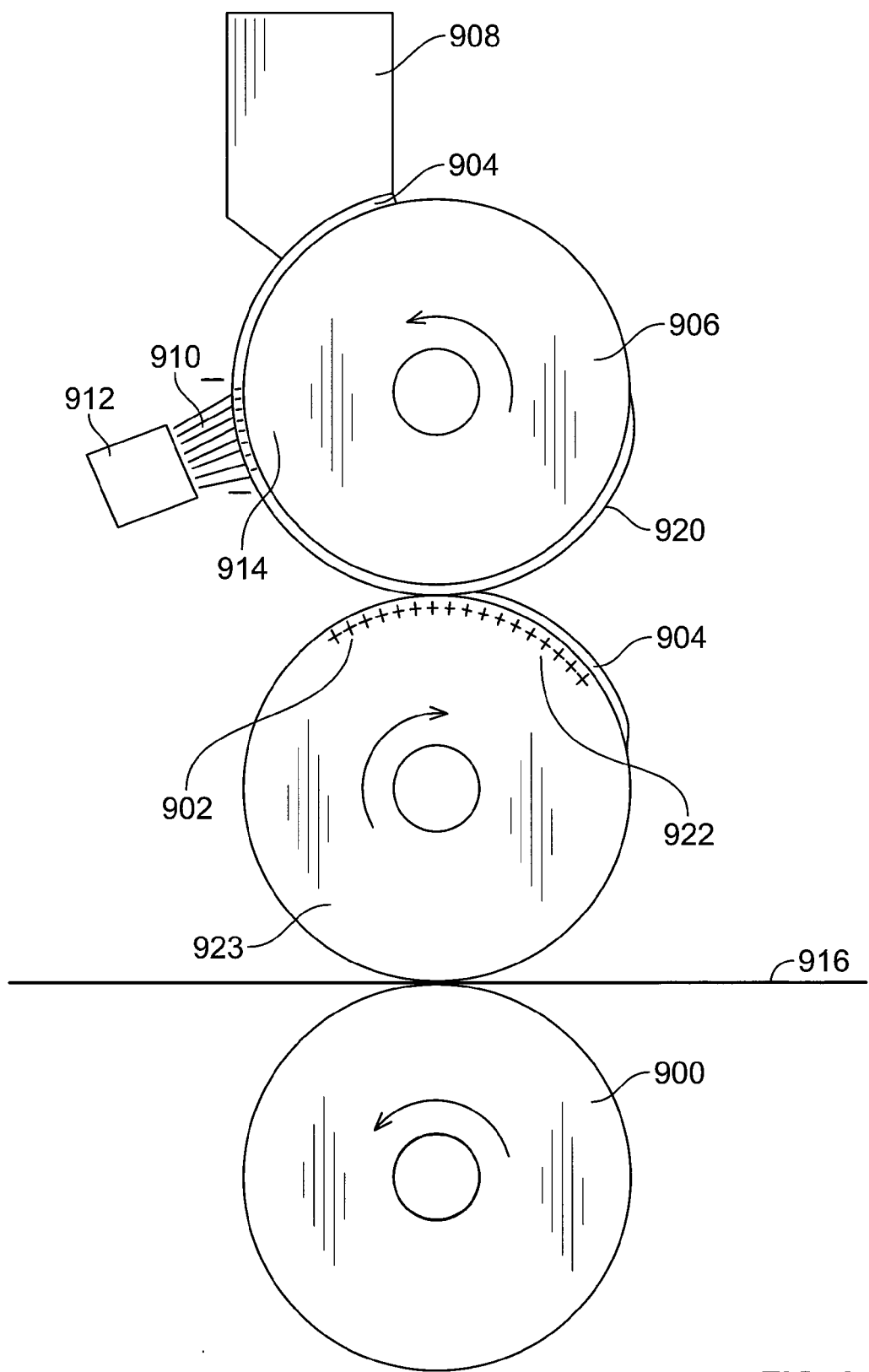

A further embodiment shown in FIG. 9 is substantially similar to the embodiment described in FIG. 8. However, in this embodiment, the substrate 916 does not pass between the impression cylinder 900 and the blanket cylinder 906. Also, a further cylinder 923 may be interposed between the blanket cylinder 906 and the impression cylinder 900. As the blanket cylinder 906 rotates, the negatively charged aqueous solution 910 that covers the pattern area 914 is attracted to a positively charged portion of the further cylinder 923 by electrostatic attraction. The negatively charged aqueous solution 910 separates from the blanket cylinder 906 pulling the principal substance 904 in the pattern area 914 thereon onto the charged area of the further cylinder 923. The substrate 916 is passed under the further cylinder 923 through a nip formed with the impression cylinder 900, and the principal substance 904 is transferred from the further cylinder 923 to the substrate 916. It is contemplated that the further cylinder 923 may have the positive charge applied thereto only in a region adjacent the blanket cylinder 906. This region has the electrostatic charge applied thereto before the principal substance 904 is transferred from the blanket cylinder 906 to the further cylinder 923. After the principal substance 904 is transferred, and as the further cylinder 923 continues to rotate, the electrostatic charge 900 may be discharged before the principal substance 904 is transferred to the substrate 916.

The embodiments described in FIGS. 8 and 9 include the further advantage of not requiring a cleaning of the blanket or the cylinder 906, 923. Preferably, all of the principal substance and negatively charged aqueous solution 910 are transferred from the blanket cylinder 906 or the cylinder 923 to the substrate 916.

Each method may include one or more intermediate steps as illustrated by the embodiment described in regard to FIG. 9. Each intermediate step may also include the application of one or more layers of the principal substance and the functional agent, for example the principal substance 904 and the negatively charged aqueous solution 910, respectively. Each intermediate step may further include a receiver surface on which the principal substance may be applied and/or collected. The final destination of the principal substance 904 may be the web of paper 916 or another substrate from where it may be collected, incubated, analyzed, and/or stored, as befits the application in question. The principal substance 904 may be applied to the web of paper 916 from the cylinder 923 or directly from the blanket cylinder 906, as shown in FIG. 8. The blanket cylinder 906 may be made of rubber or some hard, flexible material. The cylinder 923 may be a conventional plate cylinder or may be a seamless or a sleeved cylinder, as desired.

If a plate cylinder is utilized in an intermediate step to apply principal substance to the blanket cylinder 906, the plate cylinder may have principal substance 904 applied thereto from an ink train 908, which applies a principal substance. The plate cylinder may also have a silicone surface that is entirely hydrophilic that may not require wetting before the application of principal substance thereto.

As has been previously stated, certain underlying concepts embodied in the apparatuses, methods, and compositions disclosed herein may be related to the broader printing industry. As a result, certain concepts, practices, and instrumentality may be equally applicable in the present disclosure. However, the disclosure of such concepts, practices, and instrumentality does not require their use, but such disclosure merely contemplates their potential use as may be advantageous to the furtherance of the contemplated technology.

Further, rolls or cylinders having a textured surface may be used to control the application of the principal substance to the substrate, as desired. Examples of cylinders having such a textured surface are similar to a gravure cylinder having either a regular or irregular pattern of cells engraved thereon (by any known process, for example, diamond engraving, electron beam or laser engraving, acid etching, etc.) and an anilox roller used in conventional flexographic printing. In the latter case, an anilox roller with cells at a uniform or non-uniform distribution may be used. In specific examples, anilox rollers/substrates having resolutions between 600 lines per inch (lpi) and 3,500 lpi may be used, wherein the volume of each cell is related in some fashion to the drop volume of the jet heads. For example, the cell volume may be substantially equal to, more than, or less than the drop volume of the particular jet head of the patterning system. In addition, the cell volume may be selected so that the jetted material rises slightly above the cylinder surface when deposited into a cell (this may be desirable to aid in subsequent removal of the material prior to a subsequent revolution of the substrate). Still further, or in addition, the volume of the drops of, for example, functional agent, could be adjusted to control the amount of principal substance transferred into each cell.

In another example, such as for the HP jet that emits a 14 pl drop, an anilox roller/substrate may be used having a resolution of 600 lpi to accommodate the 14 pl drop size emitted by such head. Alternatively, an anilox roller/substrate having a resolution greater than or lesser than 600 lpi may be used with the HP head such that each drop emitted by the head may be deposited into multiple cells or may occupy a portion of a cell, respectively, in any event (for example, whether an anilox roller of particular resolution(s) is used or a gravure cylinder having cells of particular size(s) are used), functional agent may be selectively jetted onto the textured roll or cylinder and such agent may be retained thereon whereby lateral spreading of the functional agent may be minimized/prevented by the constraining action of the walls forming the cells, as well as the interaction between the functional agent and the surface chemistry of the substrate. Principal substance may thereafter be applied in a non-selective manner to the substrate, whereupon such principal substance associates with the functional agent, according to the affinity of the functional agent for the principal substance. The roll or cylinder may then be used to transfer the associated principal substance to a second substrate.

In these embodiments, the shape(s) and/or depths of the cells may be optimized (for example, uniform or random and larger or smaller, respectively) to the functional agent based on the surface energies of the functional agent and roll or cylinder surface and/or may be selected based upon another physical process parameter. Still further, one may use a roll or cylinder or other substrate surface with cells arranged according to a random or pseudo-random screen, if desired.

A further possible approach using a gravure or anilox cylinder or roll differs from the foregoing in that all cells may be initially indiscriminately filled with a first substance (preferably a fluid), prior to jetting a functional agent, to a level where contact with a principal substance or another substrate would not initiate contact with the principal substance or the substrate. Thereafter, selective application of a different or similar substance or a functional agent to one or more cell(s) increases the volume in such cell(s) in such a way as to enable the functional agent to contact the principal substance and selectively interact with the principal substance, for example, to filter the principal substance from a mixture of substances. In these embodiments, a small amount of jetted fluid can impact the affinity of the functional agent for the principal substance or target by allowing for variable dilution of the functional agent and/or varying the affinity of the functional agent for the principal substance or target, for example, increasing the number of targets with which the functional agent can interact.

These embodiments are illustrated in FIGS. 10A-10C, in which a substrate 1098 is created with pre-etched cells 1000 preferably, although not necessarily, in a regular (screened) pattern. After a functional agent and/or other reagent has been applied as described above, contact with a principal substance enables capture of the principal substance or target therein. In FIG. 10A, cells 1000*a*-1000*d* are filled with a first substance, such as a functional agent, a reactant, a pharmaceutical compound, or other reagent, with a meniscus (not shown) located sufficiently below an outer substrate surface 1002 to prevent contact of the cell contents with a principal substance, for example, contained within a biological and/or chemical sample, if such substrate were brought into contact with the substrate surface. One drop (FIG. 10A) or multiple drops (FIG. 10B) of a second substance (which may be different than the first substance or identical thereto) may be added to selected cells by one or more jet heads to create a meniscus in each such cell just below, even with, or slightly above the outer cylinder surface 1002 so that contact of the substrate 1098 will cause transfer of the cell contents with the other substrate. In the case of the cell 1000*b*, as shown in FIG. 10B, two or more drops 1004 may be deposited into the cell by different nozzles of one or more jet heads. In this way, a varied concentration of substance may be introduced to the cell by having a highly concentrated substance, such as a functional agent in the first drop and a compatible solvent and/or co-reactant in the second drop, which would thereby mix to form a diluted functional agent or functional agent with altered specificity for a principal substance.

A different approach is illustrated in FIG. 10B with respect to the cell 1000c, wherein multiple drops 1006 of uniform size may be deposited therein from a single nozzle. A still further methodology is shown with respect to the cell 1000d wherein multiple drops 1008 of different sizes may be deposited therein from a single nozzle. In this way, a highly controlled deposition of drops of specified composition may be introduced into substrate cells to present discrete points of contact where a principal substance may interact and/or mix with a functional agent or other reagent.

In FIG. 10C, all cells 1000a-1000d are partially or fully filled with the first substance, and negative or positive (variable) relative pressure may be used to control the amount of second fluid that may be deposited in a cell and/or to control the amount of the cell contents that may be transferred to a further substrate. A negative relative pressure may reduce the level of the first substance below the surface 1002 to a predetermined level that may confer a specific cell volume during and/or after indiscriminate application of such substance thereto. In an alternative embodiment, a positive relative pressure may be applied to the cells during application of the first substance thereto. The relative positive pressure may be removed from the cells before selective application of the second substance thereto so that the first substance in the cells settles to the bottom of the cells 1000. The second substance may be thereafter selectively added in the fashion described in connection with FIGS. 10A and 10B to raise selected cell levels to control the amount of exposure of a functional agent within the cells to control the amount of interaction, and for example, the amount of principal substance that may be drawn from a sample onto the substrate. Alternatively or in addition, the relative positive pressure may be maintained during application of the second substance and, possibly, during transfer of cell contents to the further substrate to assist in such transfer.

In a related embodiment, the first substance may be a functional agent and the second substance may be a solvent for the functional agent. Alternatively, the two substances could be functional agent alone or any two similar or dissimilar materials that mix or do not mix on contact with one another. Still further, each drop of the second substance may be large enough to flow into multiple cells, if desired. Further, in addition to altering the pressure within any particular cell, the pores 1010 in the bottom of the cells illustrated in FIG. 10C may be used to add additional reagents, functional agents, gases, principal substances, as desired per revolution or iteration of the patterning substrate containing the cells.

The functional agent may be hydrophobic or hydrophilic, depending on whether the desired result is for the functional agent to increase or decrease the association of the principal substance to the substrate surface. For example, a functional agent may include a biocide that selects only a particular cell type to adhere to a particular portion of a cell culture substrate at a particular time, which can be varied to allow multiple cell types to have varying patterns on a single substrate, as is seen in tissues.

One could further use different liquids dispensed by separate jetting devices that, when applied together, create a functional agent that has improved adherence, viscosity, and/or other desirable characteristics. The liquids may be applied at varied temperatures, pressures, flow rates, etc.

Another embodiment may include dilution of the principal substance with a fluid, for example, having a low viscosity to decrease the attractive forces of the principal substance to a surface, or in addition, a relatively high viscosity fluid to increase the attractive forces of the principal substance to a surface. Decreasing the attractive forces of the principal substance may aid in the release of the principal substance from the surface. Alternately, increasing the attractive forces may increase the binding strength between the principal substance and the substrate to impede release of the principal substance from the substrate.

Any jet system may be used to emit a functional agent or a principal substance. The functional agent and principal substance may include aqueous or non-aqueous solutions. The aqueous solution may include water, a water-soluble organic, or a combination thereof. Examples of suitable components include: a surfactant, including surfactant block copolymers, alcohols, such as methyl alcohol, ethyl alcohol, n-propyl alcohol, isopropyl alcohol, n-butyl alcohol, sec-butyl alcohol, or tert-butyl alcohol; amides, such as dimethylformamide or dimethylacetamide; carboxylic acids; esters, such as ethyl acetate, ethyl lactate, and ethylene carbonate; ethers, such as tetrahydrofuran or dioxane; glycerin; glycols; glycol esters; glycol ethers; ketones; such as acetone, diacetone, or methyl ethyl ketone; lactams, such as N-isopropyl caprolactam or N-ethyl valerolactam; lactones, such as butyrolactone; organosulfides; sulfones, such as dimethylsulfone; organosulfoxides, such as dimethyl sulfoxide or tetramethylene sulfoxide; nucleic acids, proteins, lipids, fatty acids, carbohydrates, glycoproteins, mucins, sugars, and the like, and derivatives and mixtures thereof.

Surfactant block copolymers having various properties may be used with patterning substrates, such as plates, having various material properties to achieve a patterning substrate that has selectively hydrophobic and hydrophilic surfaces. The physical bond created between the surfactant and the patterning substrate's surface may allow the patterning substrate to repeat the same pattern multiple times or to selectively vary the pattern in any given iteration of the patterning substrate, such as a revolution. By taking advantage of the material properties of the patterning substrate and block copolymer surfactants, a durable, yet variable, patterning system having the quality of known lithographic printing techniques may be achieved. Surfactants described herein may be available in various forms, for example, solid, powder, aqueous solution, gel, etc. Any desirable form may be used in accordance with the present disclosure.

Any agent may be utilized that facilitates application of a substance to a substrate. Agents having an affinity for a principal substance or a target substance within a principal substance, such that they form permanent, semi-permanent, or transitional associations and/or bonds with the principal substance and/or target substance are considered herein as functional agents. One or more functional agents may aid in the transfer of all, substantially all, or a portion of the principal substance. Functional agents and principal substances contemplated herein include, for example, a chemoattractant, a chemorepellant, a multifunctional agent, an aqueous composition, a saline solution, an intracellular cell signaling chemical, an extracellular matrix protein, a polymer, a sugar, a lipid, a micelle, a liposome, an organelle, a cell, a biological sample, a bodily fluid, an amino acid, a peptide, a protein, an antibody, an enzyme, a lectin, a sugar, a lipid, a vesicle, a salt, a small molecule, a pharmaceutical compound, a pharmaceutical prodrug, a pharmaceutical precursor, a pharmaceutical catabolite, a placebo, a nucleotide, a nucleic acid, a plasmid, a vaccine, a virus, a bacteria, a lysate, a supernatant, an inorganic salt, an antibiotic, a dye, a fluorescent compound, a chromophore, a polymer, a cytokine, a chemokine, a neurotransmitter, a steroidal hormone, a peptide hormone, a pheromone, a receptor, a coreceptor, a glycoprotein, a glycolipid, a phospholipid, an acid, a base, a catalyst, a pigment, a dye, a metal, an adjuvant, a filler, an oxidant, a reductant, a hydrophobic agent, a hydrophilic agent, a mother liquor, a toxin, and derivatives and combinations thereof. Additional examples of principal substances include, for example, lithographic inks, dyes, and metals (for example, silicon oxides, conductive metals and oxides thereof).

In one embodiment, a functional agent (or principal substance) may have a bifunctional potential, though any number of functionalities are contemplated herein. For example, the multifunctional agent may include one or more compounds each having a multifunctional potential or a plurality of compounds each having monofunctional potentials. A functional potential may include, for example, a functional portion of a compound that may be attributable to a specific chemical moiety and/or structural region of the compound that confers attachment and/or repellant properties to the compound relative to a substrate or other substance, such as, for example, a hydrophilic region, a hydrophobic region, a receptor/recognition region (for example, a paratope), an ionic region, a homologous region, a complementary region, and others known in the art. In one embodiment, one functionality confers attachment capabilities to the pattern substrate, and a second confers attachment properties to one or more principal substances that may be applied thereto.

In another embodiment, a multifunctional agent may include more than one multifunctional compound where each species of multifunctional agent has at least one functionality in common with the other multifunctional agents and at least one functionality that differs from the other multifunctional agents. In this example, a first multifunctional agent and a second multifunctional agent may each be printed onto a similar pattern substrate though the second functionalities of the first multifunctional agent and the second multifunctional agent may have different specificities for a principal substance that can be attached to either the first or the second multifunctional agents, assuming the principal substance reacts with only one type of functionality. In another embodiment, functional agents having monofunctional potentials may interact to form complexes having multifunctional potential similar to that of single multifunctional agents. In this embodiment, the monofunctional agents may be included in a single composition that may be deposited on the pattern substrate at one time, included in separate compositions deposited simultaneously, or may be contained in separate compositions that are deposited on the pattern substrate sequentially.

One example of a multifunctional agent contemplated herein includes a compound having one functionality that may be hydrophilic and a second functionality that may be hydrophobic. The multifunctional agent may be jetted in a desired pattern onto a substrate having either hydrophilic or a hydrophobic surface, whereby like functionalities between the surface and the composition would associate to attach the composition to the surface and the opposite functionality of the composition would be repelled from the surface to render a pattern of the functional agent attached thereto.

A second composition, for example, the principal substance, having a like functionality (for example, hydrophilic or hydrophobic) or otherwise attracted selectively to the second functionality of the multifunctional agent that is not attached to the surface, and that is repulsed from or otherwise not disassociated from the exposed surface of the substrate may be added to the surface by jetting, dipping, spraying, brushing, rolling, or any other manner known to a skilled artisan. Addition of the principal substance may render a pattern of the principal substance corresponding to that of the multifunctional agent, such that the principal substance may be only attached to the surface via the second functionality of the multifunctional agent.

It is further contemplated that after the application of the principal substance, one or more additional steps may be performed, including, for example a cleaning step, to ensure regiospecific attachment of the principal substance only to the second functionality of the multifunctional composition. Another contemplated step similar to the cleaning step includes a sterilization step. The principal substance may then be transferred to a second substrate, including, for example, an intermediate roller from which a pattern may be transferred to a substrate or directly to the substrate to render the desired pattern in a highly accurate and reproducible manner. In this way, selected patterns may be jetted onto a substrate using a multifunctional agent to which a principal substance may be subsequently attached that then may be transferred to and immobilized permanently or transiently on a subsequent substrate.

Additional examples of functional agents contemplated herein include polymers, including polymers having at least one hydrophilic portion and at least one hydrophobic portion, such as a poloxamer or acetylenediol ethoxylated. A poloxamer suitable for use can be represented by the formula $HO(CO_2CH_2O)_x(CH_2CHCH_3O)_y(CH_2CH_2O)_zH$, wherein x, y, and z represent integers ranging from 2 to 130, especially from 15 to 100, and x and z may be identical but chosen independently of y. Among these, there may be used: poloxamer 188, wherein x=75, y=30 and z=75, which is obtainable under the trade name Lutrol® F-68 (alternatively Pluronic® F-68) from BASF; poloxamer 185, wherein x=19, y=30 and z=19 (Lubrajel® WA from ISP); poloxamer 235 wherein x=27, y=39, and z=27 (Pluronic® F-85 from BASF); and poloxamer 238, wherein x=97, y=39 and z=97 (Pluronic® F-88 from BASF). Another particular surfactant of this type is the block copolymer poly(ethyleneoxide)-poly(propyleneoxide)-poly(ethyleneoxide), such as Pluronic® F-123 from BASF. In addition, a triblock copolymer known commercially as Pluronic® F-127 (poloxamer 407) from BASF for which x=106, y=70, and z=106 may be used. Additionally, poloxamers 101, 108, 124, 181, 182, 184, 217, 231, 234, 237, 282, 288, 331, 333, 334, 335, 338, 401, 402, and 403, respectively, may be included in the functional agent, to name a few. An acetylenediol ethoxylated suitable for use includes 3,5-dimethyl-1-hexyn-3-ol (Air Products' Surfynol® 61), and/or 2,4,7,9-tetra-methyl-5-decyne-4,7-diol (Air Products' Surfynol® 104), among others. Other surfactants suitable for use include hexadecyl trimethylammonium bromide (CTAB), polyoxyalkylene ether, and poly(oxyethylene)cetyl ether (for example, Brij® 56 or Brij® 58 from Atlas Chemicals).

Additional examples of functional agents include materials associated with the formation of self-assembled monolayers, such as alkylsiloxanes, fatty acids on oxidic materials, alkanethiolates, alkyl carboxylates, and the like. Additional contemplated components useful in functional agent solutions contemplated herein include adhesives, including water-based adhesives, water-cure adhesives, heat sensitive adhesives, and pressure sensitive adhesives, organic solvents, preservatives, scintillation fluids, colorants, such as a pigment or a dye, a scent, a polymer, a foaming agent, a gelling agent, a salt, an inorganic compound, an organic compound, water, a pH modifier, and combinations thereof.

Still further, increasing the viscosity of the functional agent and/or increasing the surface tension thereof, and/or using a supporting agent and/or mechanical structure for patterned areas can modulate spreading and transfer thus improving controllability. Other chemical and/or material science properties might be utilized to modulate this effect. Viscosity modifying agents may include propylene glycol, cellulosic materials, xanthan gum, or Johnson Polymer's Joncryl® 678, to name a few. The functional agent may also include a thixotropic fluid that changes viscosity under pressure or agitation.

Increasing surface tension of the functional agent can also reduce spreading. Surface tension modifiers can include poloxamer (for example, BASF's Pluronic®) or Air Products Surfynols®, among others. In addition, other agents may be incorporated in the functional agent composition such as anticurl and anticockle agents, litho ink modifiers, receiving surface modifier, antiseptic agents, biocides, nutrients, chemical identification tags that may differ per sample, radioisotopes, and pH adjusters and maintainers and combinations thereof.

As a still further example, a phase change of the functional agent, or the principal substance, or both, may be employed to prevent and/or promote substance transfer, collection, and or analysis. For example, functional agent may be selectively jetted onto a surface, such as a rotating disc, and principal substance may be applied to the surface having the functional agent applied thereto, whereupon the portions of the principal substance that contact the jetted functional agent may become associated therewith and converted to a gel or a solid. Alternatively, the principal substance may be applied in an indiscriminate fashion to the plate and the functional agent may thereafter be selectively applied to portions of the plate that are not to be patterned (for example, non-pattern areas), whereupon the principal substance in the jetted portions may be converted to a gel or solid upon selective reaction with the functional agent.

In another embodiment, selective reaction of a functional agent with a target within an applied principal substance, such as, binding of a paratope to an epitope may trigger a chromogenic reaction that may be monitored using a sensor or other analytical technique as known in the art. Upon detection of such reaction, the apparatus may then apply a gelling agent to the reaction site via jetting and/or via delivery through a cell pore, as in, for example, FIG. 12C. Non-gelled portions of the principal substance on the plate may be cleaned therefrom leaving only selected targets, which may be collected and/or analyzed, as desired.

Still further, a two (or more) component functional solution could be used wherein the components are individually selectively applied in succession where each is individually jettable, but which, when applied in the same location, result in a chemical or physical reaction to promote advantageous transfer, selection, binding, and/or association characteristics between, for example, at least one of the functional agent and the principal substance and the principal substance and a substrate.

Yet another modification involves the use of a phase change material to build up a surface. One example involves the use of one or more curable and removable materials as the functional agent. For example, a UV curable functional agent (or a functional agent containing a photoresist) in liquid form may be deposited on a plate and is thereafter subjected to the appropriate wavelength of light. The functional agent hardens, and principal substance is thereafter non-selectively applied to the plate. The principal substance is either attracted to or repelled by the hardened functional agent, and the resulting pattern is applied to substrate, such as a paper web. The functional agent and principal substance (if any) are then removed from the plate in preparation for subsequent patterning. This removal may be effected by washing any remaining principal substance from the plate, reversing the phase of the functional agent to a liquid, and/or removing the agent and any principal substance by washing, scraping, dissolving, and the like.

The apparatuses, methods, and compositions disclosed herein may also be relevant in industries and technologies including, for example, textiles, pharmaceuticals, biomedical, and electronics, among others. In the pharmaceutical industry, for example, the principal substance may be a drug, a therapeutic, diagnostic, or marking substance other than an ink, or a carrier for any other type of substance. In biomedical applications, for example, the principal substance may be a biological material or a biocompatible polymer. In electronics applications, the principal substance may be an electrically conductive or insulative material that may be selectively applied in one or more layers on the substrate. Other electronic applications include production of radio frequency identification ("RFID") tags on articles.

Other industries may also benefit from selective application of a principal substance to a substrate. For example, the principal substance may be a thermally conductive or insulative material. The principal substance may also be a material with enhanced absorptive, reflective, or radiative properties. Moreover, the technology could be applied to fuel cell manufacturing, and the principal substance may include functional polymers, adhesives, and three dimensional interconnect structures. Further, the principal substance may be an optical adhesive or a UV-curing polymer.

The apparatus configurations contemplated herein may enable high speed, highly accurate, selective deposition of one or more principal substances using combined multifunctional compositions and jet technologies. In this way, products including, for example, chromatographic substrates, diagnostic tests, electric chips, oligonucleotide arrays, protein arrays, cell arrays, tissue arrays, tissues, chemical arrays, drug arrays, detection systems, printed materials (for example, literature), and the like, and combination thereof may be produced in large numbers depending upon the size and set up of a given apparatus.

The functional agent may be applied directly onto the substrate or onto an intermediate surface or directly onto the principal substance disposed on a substrate using jet technology or other precisely controllable spraying or application technology. An aqueous fluid may generally have a low viscosity and a reduced propensity to form clogs, and may be therefore advantageous for use with an jet head. However, the functional agent may also be applied using jet technology in a form other than an aqueous fluid. Further, the functional agent is not limited to being a fluid at all and may be applied as a solid, for example as a thin film, a paste, a gel, a foam, or a matrix. The functional agent could comprise a powdered solid that is charged or held in place by an opposite electrostatic charge to aid in the application of the principal substance.

In one example, a liquid functional agent in the form of a solvent may be applied by one or more jet heads to a plate and a powdered principal substance may be deposited over the entire surface of the plate to form a liquid in situ in the jetted areas. Powder in the non-jetted areas may be removed (for example, by inverting the plate so that the powder simply falls off the plate, by air pressure, vacuum, centrifugal force, etc), thereby resulting in patterned and non-patterned areas. Alternatively, similar to that described above in reference to FIGS. 9 and 10, a charged powdered principal substance may be applied over an entire plate surface (or substantially the entire plate surface or only a portion of the plate surface) and may be retained on the plate by an electrostatic charge applied to the plate. The functional agent may then be jetted onto the areas to be patterned, and the electrostatic charge removed so that the powder in the non-patterned areas can be removed. In either event, the resulting pattern may thereafter be applied to a substrate, for example a web of paper or a coverslip.

As described elsewhere herein, there may be a wide variety of methods to apply a principal substance, for example a biological and/or chemical agent, to a substrate, for example a web of nitrocellulose, a membrane, a textile, a woven material, a film, an electrically conductive surface, glass, paper, a ceramic, a metal, a plastic, a tissue, a mesh, a biocompatible substrate, a gel, a rubber, a microfluidic channel, a pre-coated surface, a sterile surface, an applied principal substance, an applied functional agent, a disc, a blade, a continuous loop, a roller, a blanket roller, a hollow matrix, a three dimensional structure, and combinations thereof.

Further, the surface onto which a functional agent and/or principal substance may be patterned may vary as is known in the art. For example, the surface may be a hydrophobic surface, a hydrophilic surface, a porous surface, an electrically conductive surface, a heated surface, a cooled surface, a smooth surface, a textured surface, a concave surface, a convex surface, a surface having a channel, a surface having a raised ridge, a conical surface, a cylindrical surface, a reflective surface, a surface having a matte finish, and combinations thereof.

In alternate embodiments, the surface may be a lithographic plate, cylinder, or the like having a portion that may be used for controlling application of the principal substance to the substrate by applying variable configurations of the principal substance to the substrate. Variable symbology, encoding, addressing, numbering, or any other variable tagging technique may be utilized in a portion of a surface reserved for controlling application of the principal substance.

It may further be desirable to pair a soft patterning/blanket substrate with an opposing hard impression substrate (for example, a silicone patterning/blanket cylinder and a steel impression cylinder). Alternatively, a hard patterning/blanket substrate may be paired with a soft impression substrate (for example, a ceramic patterning/blanket cylinder and a rubber impression cylinder). In some embodiments, it may be desirable to employ a silicone patterning cylinder to create a "waterless" system. Therefore, the hardness of a surface contemplated herein may be widely variable from hard to soft and vary per region.

If a method is employed wherein a substrate does require intermediate cleaning, a cleaning solution engineered for that purpose may be selectively applied to the substrate to clean residual matter therefrom. The cleaning solution may be sprayed uniformly over the substrate as it comes around to begin a new revolution or any other type of iteration. However, it is contemplated that a cleaning solution that is applied only where desired or needed may be advantageous because such precise application results in less residual cleaning solution to collect. To facilitate precise guidance, the cleaning solution may have an electrostatic charge applied thereto interacts with an electrostatic charge applied to the substrate. The substrate may be electrostatically charged from within, for example, by a laser or an LED array.

In a further embodiment, a patterning element, such as a plate, cylinder, blanket, etc. could be selectively cleaned between patterning cycles thereof based upon the differences between successive patterns. This could be accomplished by the selective application of cleaning solution to the patterning element using one or more jet heads (which may be the same jet heads that apply functional agent to the patterning element or one or more separate heads) during the interval between application of successive patterns only to those areas where pattern changes are to occur.

A still further option is to modulate/control the temperature of one or more process parameters. For example, one might elevate the temperature of the functional agent upon application thereof to a surface to improve adherence and facilitate dispensing thereof. Alternatively, or in addition, the surface may initially be heated during application of functional agent to control adhesion, drop shape/size, and the like, and/or the surface may be chilled (or, in the case of other constituents, heated) at some point in the process once the functional agent is applied thereto so that the viscosity of the functional agent is increased, thereby reducing spread of the functional agent into non-wetted areas. Further, depending upon the application, temperature and gas regulation of the apparatus may be modulated, such as may be used during incubation. For example, a portion of a contemplated apparatus may be maintained at 37° C. and 5% $CO_2$.

Also if desired, more than one patterning element may be used to transfer an pattern and functional agent to a further surface, which, in turn, transfers the pattern and functional agent to a further substrate. Still further, functional agent may be selectively applied alone or in combination with one or more other materials to an patterning element, which, in turn applies the functional agent and other material(s) to a further patterning element that receives the principal substance. The principal substance, functional agent, and other material(s) may be transferred to the substrate by the further patterning element or another patterning element disposed between the further patterning element and the substrate. For example, a silver conductive trace may be laid down first on a cylinder, followed a resistive material followed by a semiconductor material and the combination may then be applied directly or indirectly via another patterning element to a further substrate, such as a mylar film, a paper web, a circuit board, or the like.

It will be understood that the foregoing is only illustrative of the principles of the systems and methods disclosed herein, and that various modifications can be made by those skilled in the art without departing from the scope and spirit of such systems and methods. For example, the order of some steps in the procedures that have been described may not be critical and may be changed if desired. Also, various steps may be performed by various techniques. Further, any of foregoing embodiments may be interchanged, combined, and/or excluded, as is contemplated herein.

We claim:

1. An apparatus for applying a biological component to a surface, comprising:

a first substrate;

means for jetting a functional agent onto the first substrate in a first pattern;

means for introducing a first principal substance to the functional agent and for transferring the first principal substance to a second substrate in the first pattern; and means for introducing a second principal substance to the second substrate;

wherein the first principal substance and the second principal substance undergo a biological interaction to determine a second pattern of the second principal substance associated with the second substrate, wherein one of the first principal substance and the second principal substance is a biological sample, and wherein the biological interaction is at least one of a cell surface antigen interaction, a protein-nucleic acid interaction, a nucleic acid-nucleic acid interaction, extracellular matrix protein interactions, growth factor interactions, and cell adhesion.

2. The apparatus of claim 1, wherein at least one of the first substrate and the second substrate comprises at least one of a web of nitrocellulose, a membrane, a film, an electrically conductive surface, glass, a paper, a ceramic, a metal, a plastic, a tissue, a mesh, a biocompatible substrate, a gel, a rubber, a microfluidic channel, a pre-coated surface, a sterile surface, an applied principal substance, an applied functional agent, a disc, a continuous loop, a roller, a blanket roller, a hollow matrix, and a three dimensional structure.

3. The apparatus of claim 1, wherein the second substrate comprises at least one of a hydrophobic surface, a hydrophilic surface, a porous surface, an electrically conductive surface, a heated surface, a cooled surface, a smooth surface, a textured surface, a concave surface, a convex surface, a surface having a channel, a surface having a raised ridge, a conical surface, a cylindrical surface, a reflective surface, and a surface having a matte finish.

4. The apparatus of claim 1, wherein the functional agent comprises at least one of a chemoattractant, a chemorepellant, a multifunctional agent, an aqueous composition, a saline solution, an intracellular cell signaling chemical, an extracellular matrix protein, an antibody, a sugar, a lipid, an enzyme, a cell, a biological sample, a bodily fluid, an organelle, a peptide, a protein, a vesicle, a salt, a pharmaceutical compound, a nucleotide, a nucleic acid, a plasmid, a vaccine, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a metal, an adjuvant, a filler, a hydrophobic agent, an oxidant, a reductant, and a hydrophilic agent.

5. The apparatus of claim 1, wherein the first principal substance comprises at least one of a chemoattractant, a chemorepellant, a multifunctional agent, an aqueous composition, a saline solution, an intracellular cell signaling chemical, an extracellular matrix protein, an antibody, a sugar, a lipid, an enzyme, a cell, a biological sample, a bodily fluid, an organelle, a peptide, a protein, a vesicle, a salt, a pharmaceutical compound, a nucleotide, a nucleic acid, a plasmid, a vaccine, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a metal, an adjuvant, a filler, a hydrophobic agent, and a hydrophilic agent.

6. The apparatus of claim 1, wherein the first pattern comprises at least one of a two dimensional pattern, a three dimensional pattern, a repeating pattern, a continuous pattern, an indicium, a picture, and a gradient pattern.

7. The apparatus of claim 1, wherein the second pattern comprises at least one of a two dimensional pattern, a three dimensional pattern, a repeating pattern, a continuous pattern, an indicium, a picture, and a gradient pattern.

8. The apparatus of claim 1, wherein the first substrate and the jetting means are movable relative to one another.

9. The apparatus of claim 8, wherein the first substrate is rotatable relative to the jetting means.

10. The apparatus of claim 9, wherein the first and second substrates are movable relative to one another.

11. The apparatus of claim 10, wherein the first and second substrates are rotatable relative to one another.

12. A method for applying a biological component to a surface, comprising:
jetting a functional agent onto a first substrate in a first pattern;
introducing a first principal substance to the functional agent;
transferring the first principal substance to a second substrate in the first pattern; and
introducing a second principal substance to the second substrate;
wherein the first principal substance and the second principal substance undergo a biological interaction to determine a second pattern of the second principal substance associated with the second substrate, wherein one of the first principal substance and the second principal substance is a biological sample, and wherein the biological interaction is at least one of a cell surface antigen interaction, a protein-nucleic acid interaction, a nucleic acid-nucleic acid interaction, extracellular matrix protein interactions, growth factor interactions, and cell adhesion.

13. The method of claim 12, wherein at least one of the first substrate and the second substrate comprises at least one of a web of nitrocellulose, a membrane, a film, an electrically conductive surface, glass, a paper, a ceramic, a metal, a plastic, a tissue, a mesh, a biocompatible substrate, a gel, a rubber, a microfluidic channel, a pre-coated surface, a sterile surface, an applied principal substance, an applied functional agent, a disc, a continuous loop, a roller, a blanket roller, a hollow matrix, and a three dimensional structure.

14. The method of claim 12, wherein the second substrate comprises at least one of a hydrophobic surface, a hydrophilic surface, a porous surface, an electrically conductive surface, a heated surface, a cooled surface, a smooth surface, a textured surface, a concave surface, a convex surface, a surface having a channel, a surface having a raised ridge, a conical surface, a cylindrical surface, a reflective surface, and a surface having a matte finish.

15. The method of claim 12, wherein the functional agent comprises at least one of a chemoattractant, a chemorepellant, a multifunctional agent, an aqueous composition, a saline solution, an intracellular cell signaling chemical, an extracellular matrix protein, an antibody, a sugar, a lipid, an enzyme, a cell, a biological sample, a bodily fluid, an organelle, a peptide, a protein, a vesicle, a salt, a pharmaceutical compound, a nucleotide, a nucleic acid, a plasmid, a vaccine, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a metal, an adjuvant, a filler, a hydrophobic agent, an oxidant, a reductant, and a hydrophilic agent.

16. The method of claim 12, wherein the first principal substance comprises at least one of a chemoattractant, a chemorepellant, a multifunctional agent, an aqueous composition, a saline solution, an intracellular cell signaling chemical, an extracellular matrix protein, an antibody, a sugar, a lipid, an enzyme, a cell, a biological sample, a bodily fluid, an organelle, a peptide, a protein, a vesicle, a salt, a pharmaceutical compound, a nucleotide, a nucleic acid, a plasmid, a vaccine, a small molecule, a virus, a bacteria, an inorganic salt, an antibiotic, a dye, a fluorescent compound, a polymer, a cytokine, a chemokine, a neurotransmitter, an amino acid, a receptor, a coreceptor, a glycoprotein, a glycolipid, a phospholipid, an acid, a base, a catalyst, a pigment, a metal, an adjuvant, a filler, a hydrophobic agent, and a hydrophilic agent.

17. The method of claim 12, wherein the first pattern comprises at least one of a two dimensional pattern, a three dimensional pattern, a repeating pattern, a continuous pattern, an indicium, a picture, and a gradient pattern.

18. The method of claim 12, wherein the second pattern comprises at least one of a two dimensional pattern, a three dimensional pattern, a repeating pattern, a continuous pattern, an indicium, a picture, and a gradient pattern.

19. The method of claim 12, wherein the step of jetting the functional agent further comprises a step of moving the first substrate.

20. The method of claim 19, wherein the step of moving the first substrate comprises the step of rotating the first substrate.

21. The method of claim 20, comprising the further step of moving the first and second substrates relative to one another.

22. The method of claim 21, wherein the step of moving the first and second substrates comprises a step of rotating the first and second substrates relative to one another.

* * * * *